United States Patent
Goto et al.

(10) Patent No.: US 8,731,270 B2
(45) Date of Patent: May 20, 2014

(54) MAGNETIC RESONANCE IMAGING APPARATUS AND IMAGING SLICE DETERMINATION METHOD

(75) Inventors: Tomohiro Goto, Tokyo (JP); Hisako Nagao, Tokyo (JP); Hiroyuki Itagaki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 82 days.

(21) Appl. No.: 13/377,899

(22) PCT Filed: Jun. 21, 2010

(86) PCT No.: PCT/JP2010/060423
§ 371 (c)(1),
(2), (4) Date: Dec. 13, 2011

(87) PCT Pub. No.: WO2010/150718
PCT Pub. Date: Dec. 29, 2010

(65) Prior Publication Data
US 2012/0093384 A1    Apr. 19, 2012

(30) Foreign Application Priority Data
Jun. 25, 2009 (JP) .................................. 2009-151436

(51) Int. Cl.
*G06K 9/00* (2006.01)
(52) U.S. Cl.
USPC ........................................................ 382/131
(58) Field of Classification Search
USPC ........................................................ 382/131
See application file for complete search history.

(56) References Cited

U.S. PATENT DOCUMENTS

| 5,545,993 | A | * | 8/1996 | Taguchi et al. | 324/309 |
|---|---|---|---|---|---|
| 6,556,008 | B2 | | 4/2003 | Thesen | |
| 7,190,166 | B2 | * | 3/2007 | Ikeda | 324/318 |
| 8,565,504 | B2 | * | 10/2013 | Abe et al. | 382/131 |
| 2005/0070784 | A1 | * | 3/2005 | Komura et al. | 600/410 |
| 2006/0255801 | A1 | | 11/2006 | Ikeda | |
| 2008/0169808 | A1 | | 7/2008 | Taniguchi et al. | |
| 2008/0253639 | A1 | | 10/2008 | Van Den Brink | |
| 2009/0052756 | A1 | * | 2/2009 | Saddi et al. | 382/131 |

FOREIGN PATENT DOCUMENTS

| JP | 8-289888 | 11/1996 |
|---|---|---|
| JP | 11-318849 | 11/1999 |
| JP | 2009-509613 | 3/2009 |

OTHER PUBLICATIONS

International Search Report in PCT/JP2010/060423.
European Search Report dated Jul. 8, 2013 in corresponding European Patent application No. 10792036.5.
Tomohiro Goto, et al., "Interactive scan control for kinematic study in open MRI." Magnetic Resonance in Medical Sciences, vol. 6, No. 4, 2007, pp. 241-248.

* cited by examiner

*Primary Examiner* — Samir Ahmed
*Assistant Examiner* — Totam Le
(74) *Attorney, Agent, or Firm* — Cooper & Dunham LLP

(57) ABSTRACT

In order to provide a technique for accurately realizing an examination, which is for acquiring a plurality of images of the same examination section, without a complicated operation and an extension of an examination time, body movement information of a subject is acquired immediately before each imaging in an examination, and it is determined whether or not there is a change in the position of the subject by comparing it with body movement information immediately before reference imaging. Only when there is a change in the position of the subject, an imaging slice setting image is acquired again. Then, a recommended imaging slice is calculated using the newest imaging slice setting image.

12 Claims, 23 Drawing Sheets

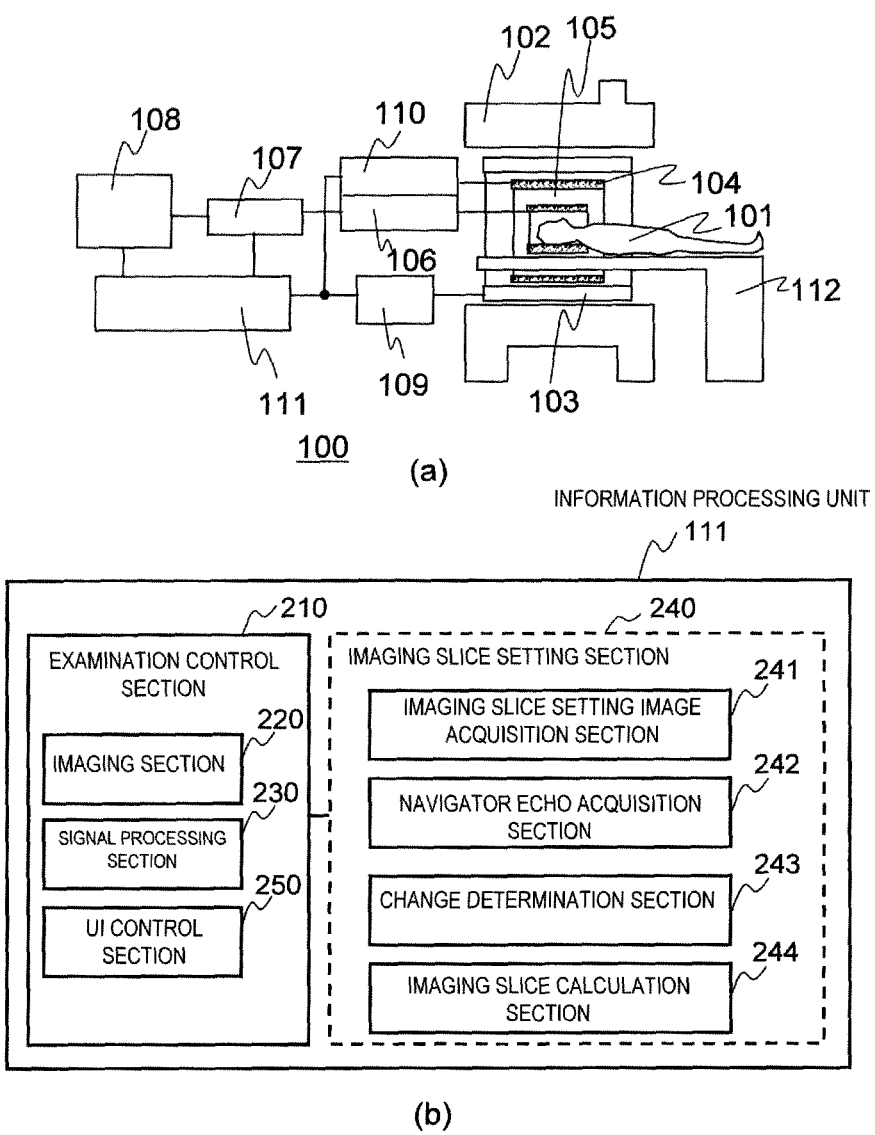

FIG. 6
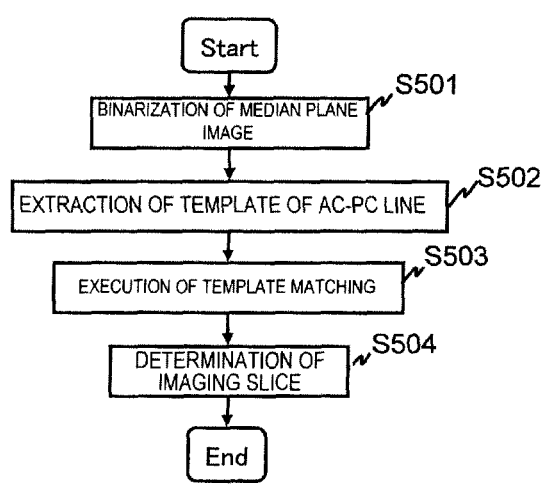
(a)
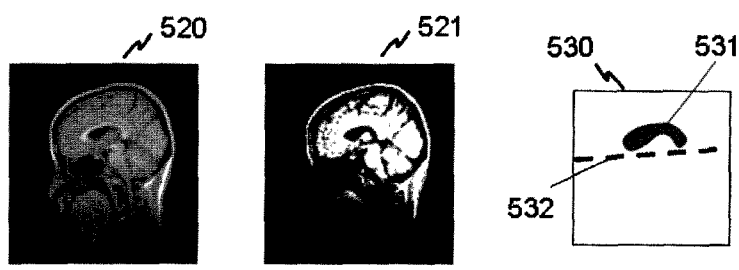
(b)

FIG. 9
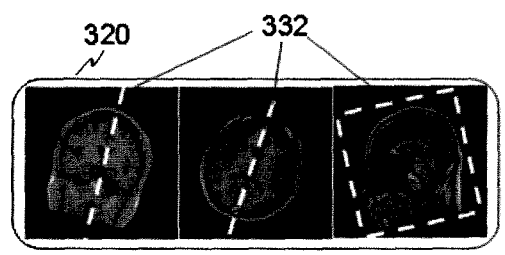
(a)
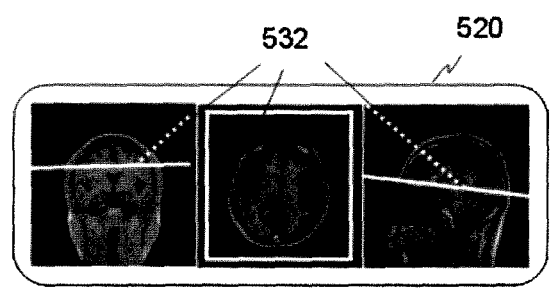
(b)

F I G . 1 2
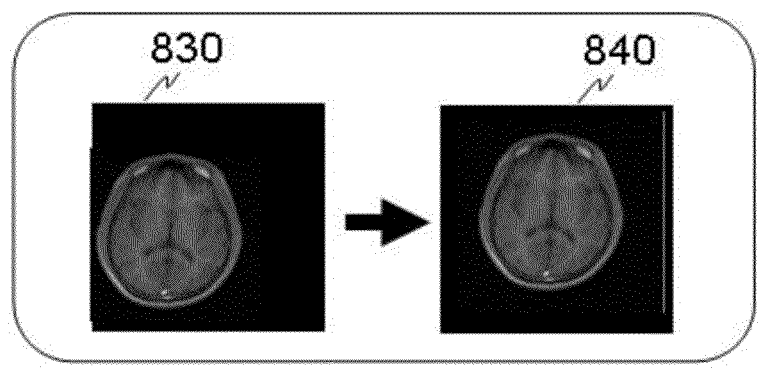

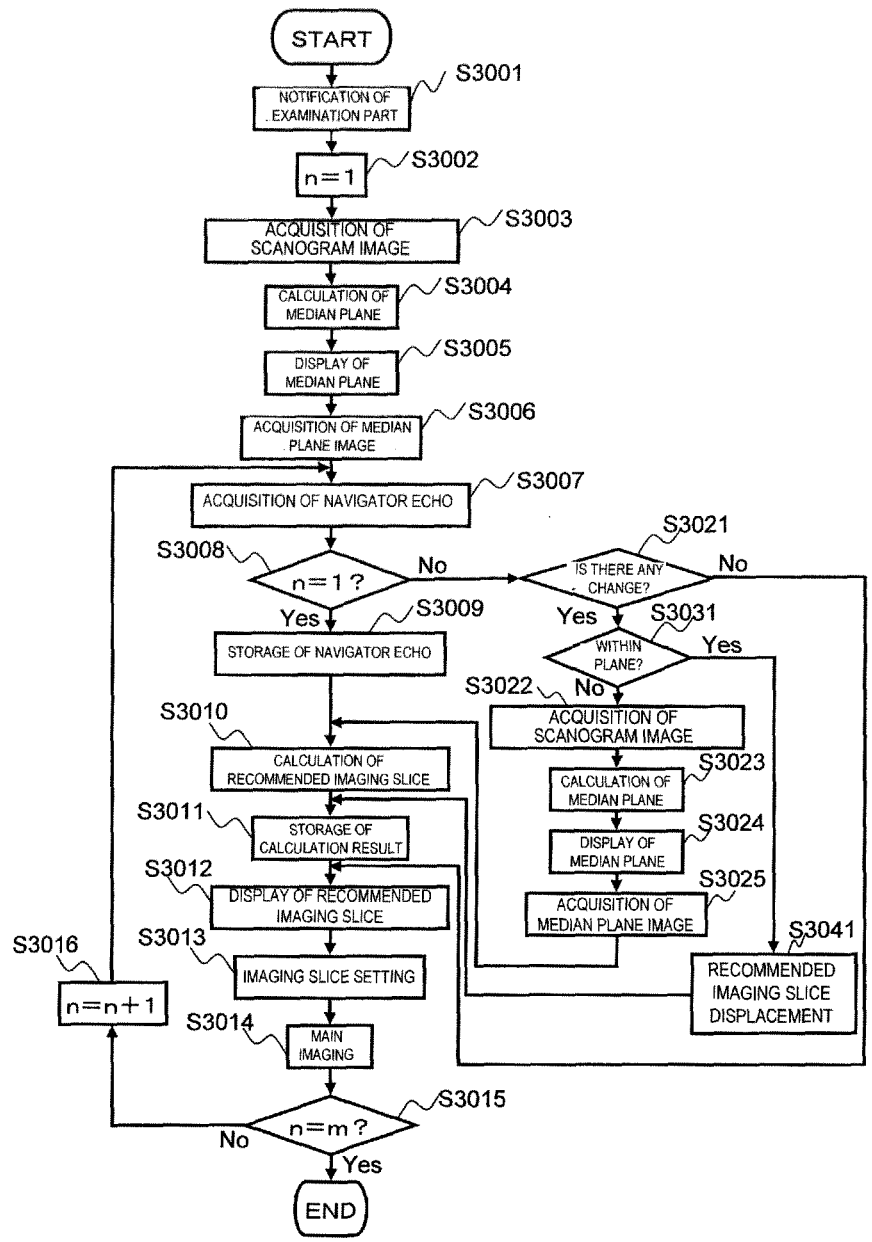

FIG. 21
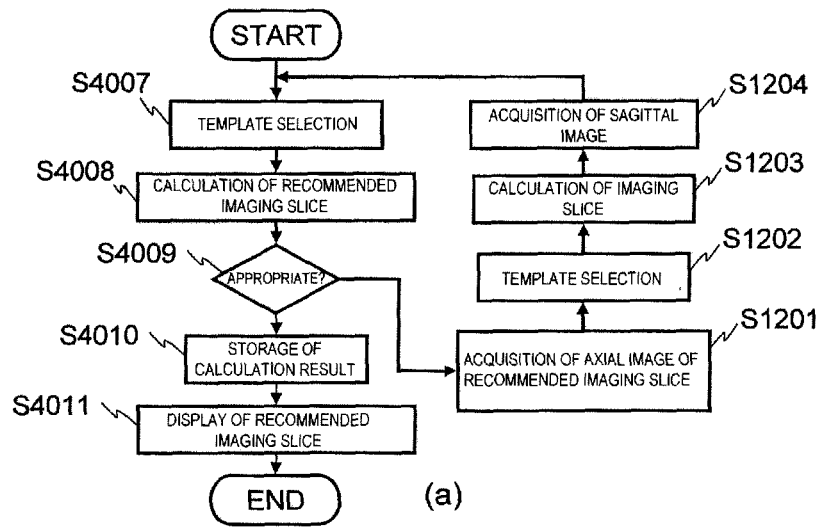
(a)
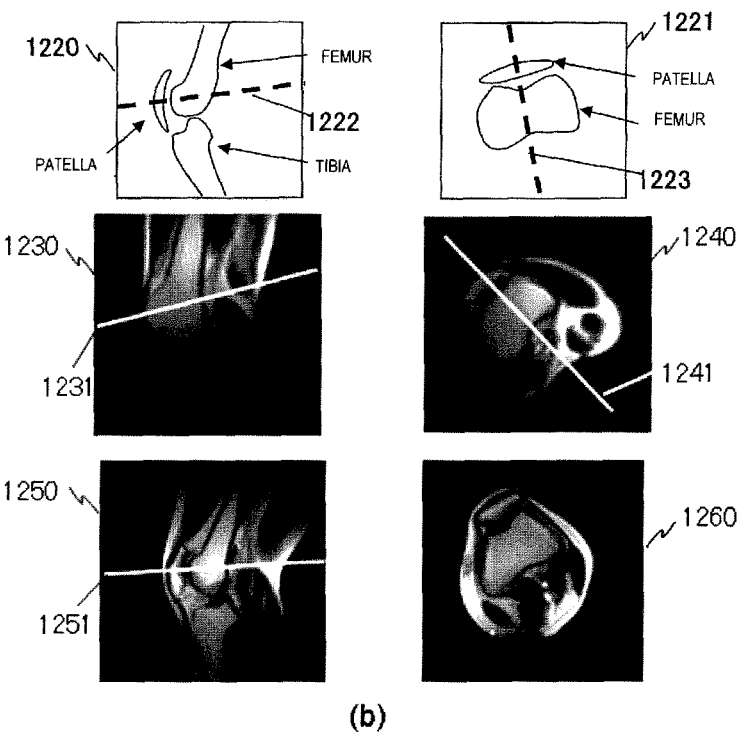
(b)

MAGNETIC RESONANCE IMAGING APPARATUS AND IMAGING SLICE DETERMINATION METHOD

TECHNICAL FIELD

The present invention relates to a magnetic resonance imaging (MRI) apparatus which measures a nuclear magnetic resonance (hereinafter, referred to as "NMR") signal from hydrogen, phosphor, or the like in a subject and images nuclear density distribution, relaxation time distribution, or the like. In particular, the present invention relates to a technique of setting automatically a cross section to be imaged.

BACKGROUND ART

In an examination using an MRI apparatus, a cross section which is anatomically determined is usually imaged for every part to be examined. This cross section is called an examination section. In the examination, this examination section is set as an imaging slice for each subject. However, since it takes skill to set the imaging slice, variations in setting may occur between operators. In particular, in a joint region with a complicated anatomical structure or the like, the setting is difficult. For this reason, a part to be examined (for example, a ligament or cartilage) may not be included in the set imaging slice. In addition, it may take a lot of time to set the imaging slice according to the skill of the operator.

In addition, for example, the same part of the same subject is continuously imaged in postoperative follow-up examinations. In such a case, it is difficult to set an imaging slice at the same position of the subject each time. In order to solve this, a function of setting an imaging slice at a desired position automatically has been proposed (for example, refer to NPL 1). NPL 1 discloses a technique of setting an imaging slice of an image for examination automatically using 3D volume data acquired in advance.

The imaging slice setting procedure herein is shown in FIG. 22. As shown in this drawing, scanogram imaging for acquiring a two-dimensional (2D) scanogram image for positioning is performed (step S1301), and then 3D volume imaging for automatic positioning which is for acquiring 3D volume data is performed in order to calculate a recommended imaging slice for main imaging (step S1302). Then, a recommended position for main imaging (recommended imaging slice) is calculated from an image acquired by this 3D volume imaging (step S1303), the recommended position for main imaging (recommended imaging slice) is displayed (step S1304), and then the main imaging is performed (step S1305).

According to the technique disclosed in NPL 1, it is possible to set the imaging slice plane without depending on the skill of the operator. However, not only the normal 2D scanogram imaging but also 3D volume imaging is needed before main imaging. For this 3D volume imaging, it takes about 2 minutes including the time to reconstruct an image from the 3D volume. Accordingly, the examination time is greatly increased.

Moreover, in the examination using an MRI apparatus, a diagnosis on the same examination section is made by comparison between images with different contrast in many cases. Therefore, in one examination, a plurality of images with different contrast are captured for the same examination section. For example, in the case of a medical checkup of the brain, a T1 weighted image, a T2 weighted image, FLAIR (or a proton density image), and a T2*weighted image are acquired using as the examination section a plane along the OM (Orbit-Meatus) line or the AC-PC (Anterior Comisure-Posterior-Comisure) line (refer to NPL 2).

CITATION LIST

Non Patent Literature

[NPL 1] Kazuaki Nakata et al., "Experience with Smart-Exam", Routine Clinical MRI, 2007, Vol. 38, No. 14, P. 55-59, Industrial Development Organization

[NPL 2] "7. Head MRI Examination", Guideline of Medical Checkup of the Brain, 2008, p. 32, The Japan Brain Dock Society

SUMMARY OF INVENTION

Technical Problem

A problem herein is when a subject moves in a state in which the examination has to some extent been done. An example is shown in FIG. 23. Here, an imaging slice (1400) for main imaging is set using three scanogram images (1401, 1402, 1403) of axial (Ax), sagittal (SAG), and coronal (COL) images. A T1 weighted image (T1W), a T2 weighted image (T2W), and a FLAIR image (FLAIR) of the set imaging slice are acquired as diagnostic images in this order. In this case, images of the same part, such as images 1411, 1412, and 1413, are acquired if the subject can hold the same position during the examination. However, if the subject moves during the examination, parts reflected on the respective contrast images are different. As a result, since images 1421, 1422, and 1423 are acquired (in this example, FLAIR (1423) is different), there is a difficulty in diagnosis.

In such a case, it is necessary to capture a scanogram image again, under the current circumstances, so that the imaging slice is reset to the same position as the imaging slice before the subject moves. In practice, it is difficult to set the imaging slice to the completely same position manually, and it may be necessary to capture all images again in some cases. A timing at which the operator recognizes that the position of the subject has changed is after the imaging is completed and image reconstruction is finished. Therefore, images which cannot be used for an examination are captured and reconstructed uselessly. When using the automatic positioning function disclosed in NPL 1 in such a case, not only scanogram imaging but also 3D volume imaging is performed for every capturing of an image with each contrast during the examination.

As described above, in the case of performing an examination of capturing a plurality of images with different contrast for the same examination section in order to make a diagnosis by comparison, it is necessary to capture images including a scanogram image again and to reset an imaging slice if the subject moves during the examination, under the current circumstances. This increases the amount of operation and imaging time. In addition, since the timing at which the operator recognizes that the position of the subject has changed is after imaging, not only is there an increase in the amount of operation and an extension of the examination time but also the operation is wasteful in many cases.

The present invention has been made in view of the above situation, and it is an object of the present invention to provide a technique for accurately realizing an examination, which is for acquiring a plurality of images of the same examination section, without a complicated operation and an extension of the examination time.

Solution to Problem

In the present invention, body movement information of a subject is acquired before each imaging in an examination, it is determined whether or not there is a change in a position of the subject by comparing it with body movement information before reference imaging, and an imaging slice setting image is acquired again when there is a change. Then, a recommended imaging slice is calculated using the newest imaging slice setting image.

Specifically, a magnetic resonance imaging apparatus includes a slice setting section which sets an imaging slice used in imaging and an imaging section which performs imaging of the imaging slice set by the slice setting section and is characterized in that the slice setting section includes a slice setting image acquisition section which acquires an imaging slice setting image for calculating a recommended imaging slice according to an examination part and an examination section, a recommended slice calculation section which calculates a recommended imaging slice on the imaging slice setting image whenever the slice setting image acquisition section acquires the imaging slice setting image, body movement information acquisition means for acquiring body movement information of a subject for every imaging, and a change determination section which determines whether or not there is a change in a position of the subject on the basis of the acquired body movement information and that the slice setting image acquisition section acquires the imaging slice setting image again when the change determination section determines that there is a change.

Advantageous Effects of Invention

According to the present invention, an examination to acquire a plurality of images of the same examination section can be accurately realized without complicated scanning and an extension of the examination time.

BRIEF DESCRIPTION OF DRAWINGS

FIG. 1(*a*) is a view showing the device configuration of an MRI apparatus of a first embodiment, and FIG. 1(*b*) is a functional block diagram of an information processing unit of the MRI apparatus of the first embodiment.

FIG. 6 is a view for explaining recommended imaging slice calculation processing of the first embodiment, where FIG. 6(*a*) is the process flow and FIG. 6(*b*) is examples of a template and an image.

FIG. 9 is examples of a scanogram image and a median plane image when the AC-PC line of the head of the first embodiment is an examination section.

FIG. 12 is a view for explaining processing of another example of the examination processing of the first embodiment.

FIG. 13 is a process flow of another example of the examination processing of the first embodiment.

FIG. 21 is a view for explaining processing of re-acquiring an imaging slice setting image of the second embodiment, where FIG. 21(*a*) is the process flow and FIG. 21(*b*) is examples of a template and an acquired image.

DESCRIPTION OF EMBODIMENTS

First Embodiment

Figure 2:
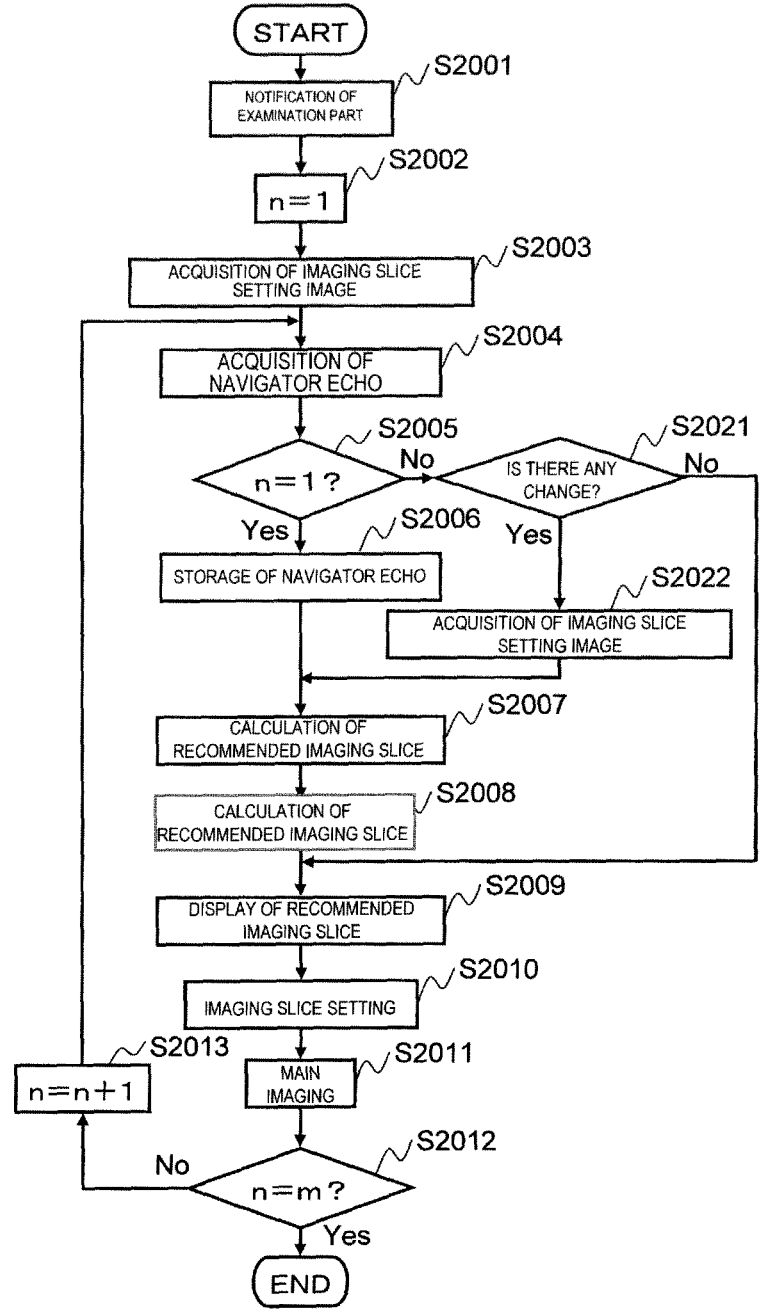
FIG. 2 is a process flow of examination processing of the first embodiment.

Hereinafter, a first embodiment to which the present invention is applied will be described. Hereinafter, in all drawings for explaining the embodiments of the present invention, the same reference numeral is given to elements with the same function, and repeated explanation thereof will be omitted.

First, a magnetic resonance imaging apparatus (hereinafter, referred to as an MRI apparatus) of the present embodiment will be described. FIG. 1(*a*) is a view showing the configuration of an MRI apparatus 100 of the present embodiment. As shown in this drawing, the MRI apparatus 100 of the present embodiment includes: a static magnetic field generator 102 which generates a static magnetic field in the imaging space; a bed 112 on which a subject 101, such as a patient, is placed so that the subject 101 is disposed in the imaging space; an RF coil 104 which applies a high-frequency magnetic field (RF) pulse to the subject 101; an RF probe 105 for detecting a nuclear magnetic resonance (NMR) signal generated by the subject 101; and a gradient magnetic field coil 103 which generates gradient magnetic fields in X, Y, and Z directions in the imaging space. In addition, the MRI apparatus 100 includes a gradient magnetic field power source 109, an RF transmitter 110, a signal detector 106, an information processing unit 111, a display unit 108, and an operating unit 107.

The gradient magnetic field power source 109 transmits a signal to the gradient magnetic field coil 103 and generates a gradient magnetic field in each direction. The gradient magnetic field is for giving positional information to an echo signal. For example, different phase encoding is given by a phase encoding gradient magnetic field on the imaging slice plane selected by a slice selection gradient magnetic field, and an echo signal obtained by each phase encoding is detected while applying a read gradient magnetic field. As the number of the phase encoding, the value of 128, 256, 512, or the like per image is usually selected.

The RF transmitter 110 transmits a signal to the RF coil 104 and generates an RF pulse, and includes a high-frequency oscillator, a modulator, and a high-frequency amplifier. The RF pulse output from the high-frequency oscillator is amplitude-modulated by the modulator at a timing according to a command from the information processing unit 111 and then the amplitude-modulated high-frequency magnetic field pulse is amplified by the high-frequency amplifier and is supplied to the RF coil 104.

The signal detector 106 detects an NMR signal (echo signal) detected by the RF probe 105. In addition, each echo signal is usually acquired as a time-series signal including 128, 256, 512, or 1024 items of sampling data. The acquired signal (data) is subjected to a two-dimensional Fourier transform by the information processing unit 111 and is reconstructed as one MR image.

The display unit 108 and the operating unit 107 are user interfaces. The display unit 108 displays the acquired image signal as an image. For example, a processing result of the information processing unit 111 is displayed. In addition, an operator inputs information required for the processing in the information processing unit 111 through the operating unit 107.

The information processing unit 111 realizes imaging by converting the echo signal detected by the signal detector 106 into an image signal by signal processing or calculation as described above and also by controlling the operations of the gradient magnetic field power source 109, the RF transmitter 110, and the signal detector 106 according to the imaging sequence set in advance. This imaging sequence is determined by a pulse sequence, which determines the procedure of application of the RF pulse and the gradient magnetic field and echo signal detection, and imaging parameters, which determine these timing, intensity, repetition time, and the like.

A functional block diagram of the information processing unit 111 of the present embodiment is shown in FIG. 1(*b*). The information processing unit 111 of the present embodiment includes an examination control section 210 which controls the flow of the entire examination. The examination control section 210 includes: an imaging section 220 which realizes imaging by controlling each section according to the imaging sequence; a signal processing section 230 which processes the detected echo signal and performs various kinds of operations, such as image reconstruction; and a user interface (UI; an interface between each of these sections and the display unit 108 and the operating unit 107) control section 250.

The UI control section 250 receives information required for executing the examination from the operator and displays on the display unit 108 the result of the processing performed according to the control of the examination control section 210. In the present embodiment, the UI control section 250 receives an input of an examination part and an examination section and notifies each processing section of it, for example. In addition, the UI control section 250 performs various kinds of calculation processing on a result processed by other functions.

In addition, the information processing unit 111 includes a CPU, a memory, and a storage device. Each function of the information processing unit 111 is realized when the CPU loads a program stored in the storage device to the memory and executes it. In addition, data required for executing the processing of each function, data acquired by processing, pulse sequence, and data input through the operating unit 107 are stored in the storage device. In addition, data acquired during the execution of each processing is also stored temporarily. In addition, a function of at least one section of the information processing unit 111 may be configured on a general-purpose information processing apparatus provided separately from the MRI apparatus 100.

A current object to be imaged by the MRI is a proton which is widely used clinically and which is a main component material of the subject that is the subject 101. The shapes or functions of the head, abdomen, limbs, and the like of the human body are imaged in a two-dimensional or three-dimensional manner by imaging the spatial distribution of proton density or the spatial distribution of excited-state relaxation.

Meanwhile, for the echo signal, there are tissue-specific parameters called a T1 value and a T2 value. By capturing images with different contrast called a T1 weighted image and a T2 weighted image on which these are reflected, it is possible to distinguish the living tissue and further to determine whether or not the tissue is a lesion (for example, a tumor). This is because the parameters called the T1 value and the T2 value change because of tissue state changes, such as a disease. These images with different contrast can be acquired by changing the setting of the pulse sequence repetition time TR and the echo signal acquisition timing TE among the imaging parameters.

Generally, imaging is performed by designating an examination section, which is specified by the anatomical characteristic structure, as an imaging slice for each part. Moreover, generally, an imaging slice setting image through which an imaging slice can be set is acquired by performing scanogram imaging, and the imaging slice is set on the imaging slice setting image. In the present embodiment, a plurality of images with different contrast of the same examination section are acquired in one examination. That is, the above-described imaging sequence is executed multiple times in one examination to acquire images.

Since an imaging slice is specified on the coordinate system unique to the MRI apparatus 100 and the examination section is specified by the anatomical characteristic structure of the subject 101, the subject 101 is a reference. Accordingly, in the case of performing imaging multiple times as in the present embodiment, if the subject 101 is displaced during the examination, an imaging slice determined so as to match the examination section at the initial position of the subject 101 is shifted from the examination section of the subject 101 at that point of time. In the related art, it is not possible to recognize this shift, and this shift is first recognized through the finally acquired image. Accordingly, the imaging is done again. In addition, in each imaging, an imaging slice matching the examination section at that point of time needs to be set. For this reason, the total examination time becomes long.

In the present embodiment, in order to solve such a problem, a navigator echo is acquired in each imaging during an examination to determine whether or not the position of the subject 101 has been changed, and the imaging slice is adjusted according to it.

In order to realize these functions, the examination control section 210 of the present embodiment calculates a recommended imaging slice which is an imaging slice recommended according to the examination part and the examination section, which are designated through the UI control section 250, by the imaging section 220, the signal processing section 230, and the UI control section 250 and realizes an imaging slice setting section 240 displayed on the UI control section 250. The imaging slice setting section 240 includes: an imaging slice setting image acquisition section 241 which acquires an image for imaging slice setting; a navigator echo acquisition section 242 which acquires a navigator echo by an instruction of the examination control section 210; a change determination section 243 which determines whether or not the position of subject 101 has been changed on the basis of the navigator echo; and an imaging slice calculation section 244 which calculates an imaging slice for main imaging on the imaging slice setting image by an instruction of the examination control section 210.

In addition, the information processing unit 111 has various kinds of data, which are required when the examination control section 210 executes an examination, in its own storage device. In the present embodiment, for example, a template used for imaging slice setting and a scanogram imaging slice for performing scanogram imaging are stored. The template and the scanogram imaging slice are stored so as to match the examination part and the examination section. In addition, data under processing is also stored in the storage device.

Hereinafter, the flow of an examination of the present embodiment will be described. Here, in an examination in which imaging is performed multiple times, an imaging slice matching the examination section is set for every imaging. FIG. 2 is a process flow of examination processing of the present embodiment. In addition, the following examination is executed according to the control of the examination control section 210 of the present embodiment. In addition, n (n is a positive integer) is a counter which counts the number of times of imaging. In addition, it is assumed that imaging is performed m (m is a positive integer) times herein.

The UI control section 250 receives a designation of an examination part (and an examination section) from an operator (step S2001). The examination control section 210 starts examination processing according to the designation reception of the UI control section 250. First, the examination control section 210 sets the counter n to 1 (step S2002) and makes the imaging slice setting section 240 set an imaging slice.

Specifically, the imaging slice setting section 240 makes the imaging slice setting image acquisition section 241 acquire an imaging slice setting image according to the examination part and the examination section accepted by the UI control section 250 (step S2003). Then, the imaging slice setting section 240 makes the navigator echo acquisition section 242 acquire a navigator echo (step S2004). Here, the imaging slice setting section 240 determines the number of times of imaging (step S2005). If the imaging is first imaging, the acquired navigator echo is stored (step S2006). Then, the imaging slice setting section 240 makes the imaging slice calculation section 244 calculate a recommended imaging slice for main imaging on the imaging slice setting image (step S2007), stores the calculation result in the storage device as a first recommended imaging slice (step S2008), and displays it as a recommended imaging slice on the display unit 108 through the UI control section 250 (step S2009).

Then, the imaging slice setting section 240 waits for an instruction from the operator to set the recommended imaging slice as an imaging slice (step S2010).

In response to the imaging slice setting of the imaging slice setting section 240, the examination control section 210 executes main imaging in the imaging slice (step S2011).

Then, the examination control section 210 determines whether or not all imaging, which is due to be performed in the examination, has been executed (step S2012). If all imaging is finished, the processing ends. On the other hand, if all imaging is not finished, the counter n is incremented by 1 (step S2013), and the process returns to step S2004.

In addition, when it is determined that the imaging is not the first imaging in step S2005, the imaging slice setting section 240 makes the change determination section 243 determine whether or not the position of the subject 101 has been changed (step S2021). Here, when it is determined that there is no change, the process proceeds to step S2009 in which the first imaging slice stored in the storage device is displayed as a recommended imaging slice as it is. On the other hand, when it is determined that there is a change in step S2021, the imaging slice setting section 240 makes the imaging slice setting image acquisition section 241 acquire an imaging slice setting image (step S2022). Then, the process proceeds to step S2007 in which the imaging slice calculation section 244 is made to calculate an imaging slice for main imaging on the newest imaging slice setting image.

Hereinafter, processing in each step will be described in detail. Here, a case of performing an examination having a general AC-PC line as an examination section in the head examination will be described as an example. The examination control section 210 starts an examination when the operator inputs the head AC-PC line and the examination part through an interface for examination part input which is set in advance.

The imaging slice setting image acquisition processing by the imaging slice setting image acquisition section 241 in steps S2003 and S2022 will be described. When an instruction to start the processing is received, the imaging slice setting image acquisition section 241 of the present embodiment performs scanogram imaging on the scanogram imaging slice, which is stored in the storage device so as to match the examination part (and the examination section) notified through the UI control section 250, according to the imaging sequence for scanogram imaging set in advance. As a result, a scanogram image of a part to be examined is acquired. As the scanogram image, axial, coronal, and sagittal images of the part to be examined are acquired. When the examination section of the part to be examined can be set on any of these images, these scanogram images are set as imaging slice setting images. In addition, the imaging slice setting image acquisition section 241 acquires a scanogram image by making the imaging section 220 perform scanogram imaging and making the signal processing section 230 reconstruct an image from the echo signal.

Here, the AC-PC line of the head is set on a median plane image. The median plane is none of the scanogram images. For this reason, when the operator inputs an AC-PC line as the examination section for the head as an imaging part, the imaging slice setting image acquisition section 241 further performs median plane calculation processing for calculating the median plane, which is an imaging slice setting section, using the acquired scanogram image. In addition, a median plane image is acquired by performing imaging with the calculated median plane as an imaging slice. In addition, this median plane image is set as an imaging slice setting image.

Figure 3:
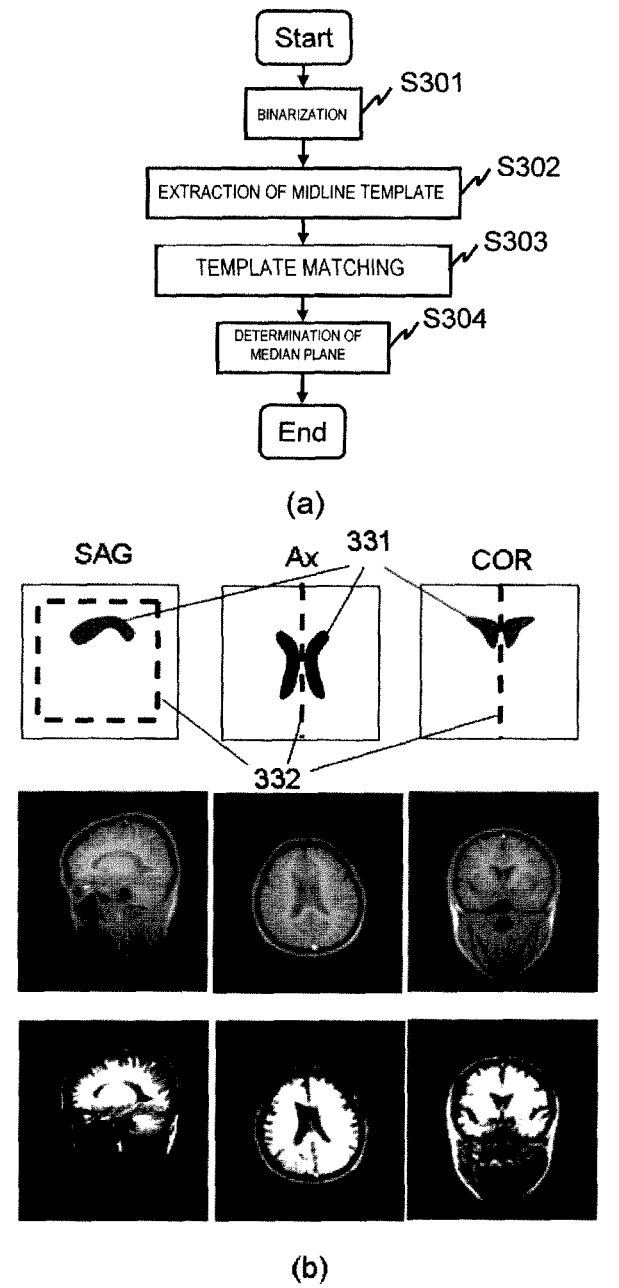
FIG. 3 is a view for explaining median plane calculation processing of the first embodiment, where FIG. 3(*a*) is the process flow and FIG. 3(*b*) is examples of a template and an image.

In addition, a template matching method is used to calculate the median plane. Here, processing of calculating the median plane by the imaging slice setting image acquisition section 241 of the present embodiment will be described. FIG. 3 is a view for explaining the median plane calculation processing of the present embodiment. FIG. 3(a) is a process flow of the median plane calculation processing. In addition, FIG. 3(b) is examples of a median plane template 330, a scanogram image 320, and a binarized image 321 obtained by binarizing the scanogram image 320, all of which are used for matching.

As shown in FIG. 3(b), the median plane template 330 is a pattern which specifies the shape of a characteristic part (331), which is called the corpus callosum and the cerebral ventricle whose shapes can be easily recognized, and the positional relationship between the characteristic part 331 and a median plane 332 on the respective sagittal (SAG), axial (Ax), and coronal (COR) images. The median plane template 330 is created in advance on the basis of a scanogram image captured in advance and is stored in the storage device so as to match the examination part (and the examination section), for example.

First, the imaging slice setting image acquisition section 241 binarizes the acquired scanogram image 320 to acquire the binarized image 321 (step S301). Then, the median plane template 330 is extracted from the template group stored in the storage device (step S302). Then, template matching processing between the binarized image 321 and the template 330 is performed (step S303).

Here, general template matching processing is used as the matching processing. First, the sizes of the binarized image 321 and the template 330 are made to match each other. Size matching is realized by performing zero filling in the k space for the data with a smaller size. The data with a smaller size is disposed in the middle of the matrix specified by the larger data size and zero data is filled in the surrounding data missing portion. Then, the data is reconstructed by a Fourier transform. When the binarized image 321 is small, the data is reconstructed by performing zero filling in a state before the Fourier transform. On the other hand, when the template 330 is small, the data is reconstructed by performing zero filling after performing an inverse Fourier transform. In addition, the size matching may also be realized by simply enlarging or reducing the template 330.

After size matching between the binarized image 321 and the template 330, D expressed by the following Expression (1) or Expression (2) is calculated while moving the median plane template 330 by one pixel at a time on the scanogram image 321 after binarization, for example, and the position at which D becomes smallest is set as the matching state.

$$D = \Sigma_{K=1}^{n}(P_{i,k}-P_{j,k})^2 \quad (1)$$

$$D = \Sigma_{k=1}^{n}|P_{i,k}-P_{j,k}| \quad (2)$$

Here, $P_i=(P_{i,1}, P_{i,2}, P_{i,n})$ indicates a density value of each point of the template 330, and $P_j=(P_{j,1}, P_{j,2}, P_{j,n})$ the density value of each point of a scanogram image 321 after binarization.

The median plane 332 on the template 330 of the position of the matching state is determined as a median plane on the scanogram image 320 (step S304).

Through the above procedure, the imaging slice setting image acquisition section 241 of the present embodiment calculates a median plane when the head is set as an imaging part and the AC-PC line is set as an examination section. In addition, as described above, a median plane image is acquired with the calculated median plane as an imaging slice, and this is set as an imaging slice setting image. In this case, the imaging slice setting image acquisition section 241 makes the signal processing section 230 perform median plane calculation processing, makes the imaging section 220 execute scanogram imaging with the median plane as an imaging slice, and makes the signal processing section 230 reconstruct an image of the median plane from the acquired echo signal.

Next, navigator echo acquisition processing by the navigator echo acquisition section 242 in the above step S2004 will be described. When an instruction is received from the imaging slice setting section 240, the navigator echo acquisition section 242 acquires a navigator echo stored in advance so as to match an examination part (and an examination section). In the present embodiment, the navigator echo acquisition section 242 acquires navigator echoes (a 2D navigator image and a 3D navigator image) of 2D and/or 3D images and navigator echoes in three axial directions perpendicular to each other, that is, in an x-axis direction, a y-axis direction, and a z-axis direction according to the known imaging sequence for navigator echo acquisition. For example, an acquisition time when acquiring a 2D navigator image of 64×64 using the imaging sequence of TR=4 ms is 256 ms. Even if the 2D navigator image is acquired for the three cross sections perpendicular to each other, the acquisition time is about 0.7 seconds.

In addition, an acquisition time when acquiring one echo in each axial direction without applying the phase encoding gradient magnetic field is about tens of milliseconds. Therefore, there is almost no extension of the examination time due to navigator echo acquisition processing.

In addition, the navigator echo acquisition section 242 acquires a 2D/3D navigator image by making the imaging section 220 execute the imaging sequence for navigator echo acquisition and making the signal processing section 230 reconstruct the acquired echo signal.

Figure 4:
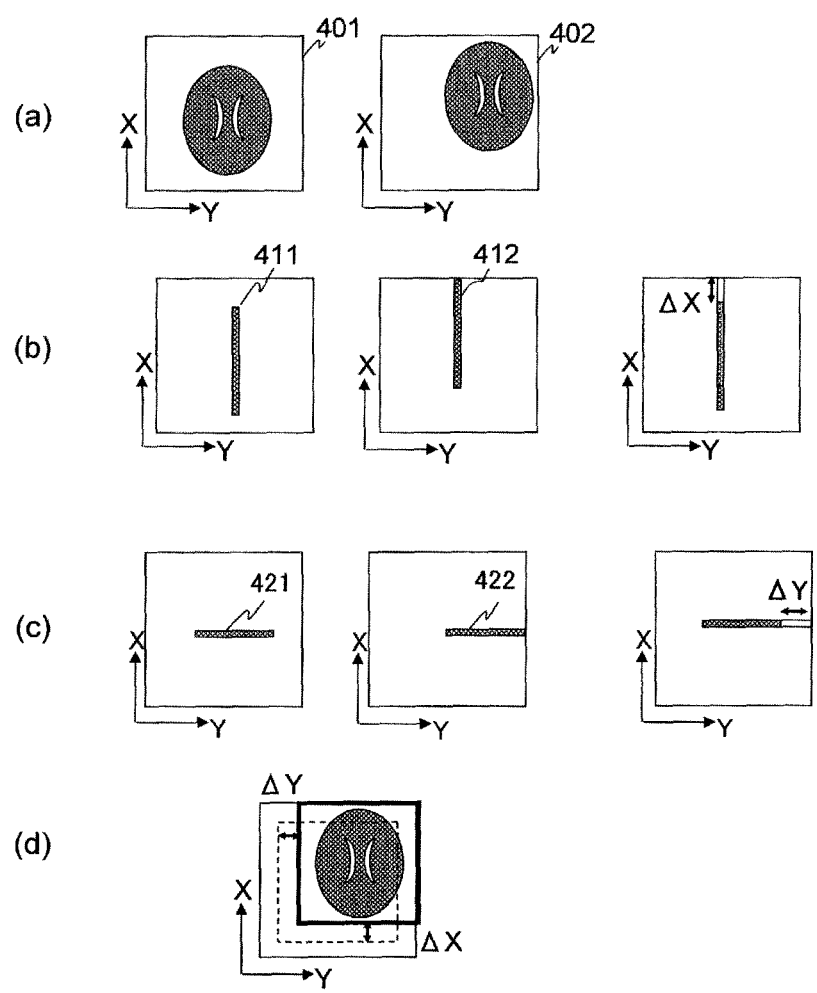
FIGS. 4(*a*) to 4(*d*) are views for explaining change determination processing of the first embodiment.
Figure 5:
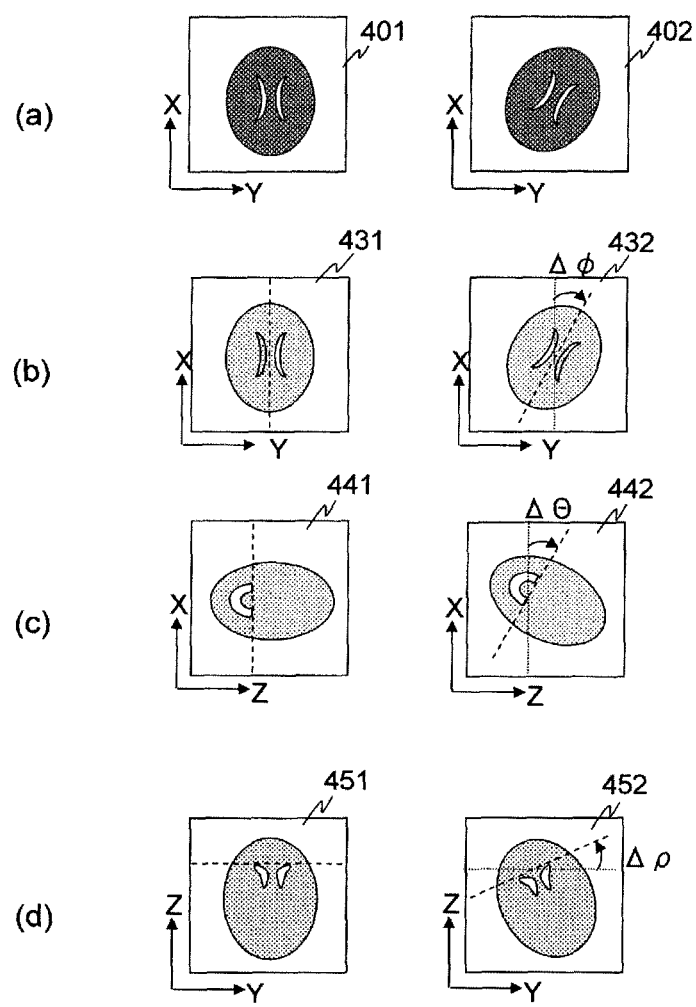
FIGS. 5(*a*) to 5(*d*) are views for explaining change determination processing of the first embodiment.

Next, change determination processing by the change determination section 243 in the above step S2021 will be described. FIGS. 4 and 5 are views for explaining the change determination processing of the present embodiment. The change determination section 243 compares a navigator echo acquired immediately before each imaging with a navigator echo acquired at the reference to determine whether or not the position of subject 101 has been changed. The change determination section 243 of the present embodiment sets the navigator echo acquired immediately before the first imaging as a reference navigator echo, and detects the amount of parallel movement in the position change from the navigator echoes in the three axial directions (x-axis direction, y-axis direction, and z-axis direction) and detects the amount of rotational movement in the position displacement from the 2D navigator images of the three cross sections perpendicular to each other. In addition, the change determination section 243 makes the signal processing section 230 perform the following change determination processing from the acquired navigator echoes or the acquired 2D navigator images.

First, detection of the amount of parallel movement will be described using FIG. 4. As shown in FIG. 4(a), the change determination section 243 determines whether or not there is a change in each of the x-axis direction, the y-axis direction, and the z-axis direction between a position 401 immediately before the first imaging and a position 402 of the subject 101 immediately before n-th imaging. Here, the amount of displacement is separately calculated for each of the x-axis direction, the y-axis direction, and the z-axis direction. Specifically, the change determination section 243 performs a correlation calculation while shifting the absolute value data, which is obtained by the Fourier transform in the navigator echo acquisition direction, by one pixel at a time and sets the amount of pixel shift when the correlation coefficient becomes greatest as a variation of the position of the subject 101 in the navigator echo acquisition direction. Here, only a change on the xy plane will be considered and described for convenience of explanation.

FIG. 4(b) shows a situation when calculating a variation Δx in the x-axis direction. The amount of shift in which the correlation coefficient becomes greatest is searched for by performing a correlation calculation while shifting absolute value data 411, which is obtained by performing a Fourier transform in the x direction for the x-axis-direction navigator echo acquired immediately before the first imaging, and absolute value data 412, which is obtained by performing a Fourier transform in the x direction for the x-axis-direction navigator echo acquired immediately before the n-th imaging, in the x direction by one pixel at a time. Then, the acquired amount of shift is set to the amount of displacement Δx in the x direction.

FIG. 4(c) shows a situation when calculating a variation Δy in the y-axis direction. The amount of shift in which the correlation coefficient becomes greatest is searched for by performing correlation calculation while shifting absolute value data 421, which is obtained by performing a Fourier transform in the y direction for the y-axis-direction navigator echo acquired immediately before the first imaging, and absolute value data 422, which is obtained by performing a Fourier transform in the y direction for the y-axis-direction navigator echo acquired immediately before the n-th imaging, in the y direction by one pixel at a time. Then, the acquired amount of shift is set to the amount of displacement Δy in the y direction.

As described above, the amount of displacement Δy in the y-axis direction and the amount of displacement Δx in the x-axis direction are separately calculated, and the displacement on the xy plane is specified as shown in FIG. 4(d).

Next, detection of the amount of rotational movement will be described using FIG. 5. As shown in this drawing, the change determination section 243 of the present embodiment determines whether or not there is a change between the position 401 of the subject 101 immediately before the first imaging and the position 402 of the subject 101 immediately before the n-th imaging by comparing a 2D navigator image of each cross section and a navigator echo in each axial direction acquired by the first imaging with a 2D navigator image of each cross section acquired immediately before the n-th imaging.

Matching processing is performed by rotating by a predetermined angle either each of a navigator echo image 431 of the axial plane (xy plane), a navigator echo image 441 of the sagittal plane (zx plane), and a navigator echo image 451 of the coronal plane (yz plane), which are acquired immediately before the first imaging, or a navigator echo image 432 of the axial plane (xy plane), a navigator echo image 442 of the sagittal plane (zx plane), and a navigator echo image 452 of the coronal plane (yz plane), which are acquired immediately before the n-th imaging. A method, such as the template matching processing described in the median plane calculation processing, is used for the matching processing. In addition, the rotation angles Δϕ, Δθ, and Δρ in the matching state are assumed to be the amounts of rotational movement within the respective planes.

As described above, the amount of parallel movement (Δx, Δy, Δz) and the amount of rotational movement (Δϕ, Δθ, Δρ) are calculated, and each is compared with a threshold value set in advance. Then, when at least one exceeds the threshold value, the change determination section 243 determines that there is a change in the position of the subject 101. On the other hand, when all values are equal to or smaller than the corresponding threshold values, the change determination section 243 determines that there is no change in the position of the subject 101. In addition, although both the navigator echo of the 2D and/or 3D image and the navigator echo in the three axial directions perpendicular to each other are acquired and both the amount of parallel movement and the amount of rotational movement are detected herein, the present invention is not limited to this. Only one of them may be acquired, and only one of the amounts of movement may be detected.

Next, recommended imaging slice calculation processing by the imaging slice calculation section 244 in the above step S2007 will be described. The imaging slice calculation section 244 calculates an imaging slice for main imaging on the imaging slice setting image and stores the result in the storage device and also displays it on the display unit 108 as a recommended imaging slice. In the present embodiment, the imaging slice calculation section 244 calculates an imaging slice by binarizing the imaging slice setting image and performing matching with a template which specifies the positional relationship between the characteristic part and the imaging slice.

FIG. 6 is a view for explaining the recommended imaging slice calculation processing of the present embodiment. FIG. 6(a) is a process flow of the recommended imaging slice calculation processing, and FIG. 6(b) is examples of an imaging slice setting image 520, its binarized image 521, and an AC-PC line template 530 used for matching.

As shown in FIG. 6(b), the AC-PC line template 530 is a pattern which specifies, on the imaging slice setting image (here, a median plane image), the shape of the characteristic part 531 and the positional relationship between the characteristic part 531 and the examination section (here, AC-PC line) 532 set as an imaging slice. The AC-PC line template 530 is created in advance on the basis of a scanogram image captured in advance and is stored in the storage device so as to match the examination part (and the examination section).

The imaging slice calculation section 244 specifies an examination section (here, AC-PC line) on the binarized image 521 by matching the image (binarized image) 521, which is obtained by binarizing the imaging slice setting image (here, a median plane image) 520, with the AC-PC line template 530. In addition, the flow of recommended imaging slice calculation processing is basically the same as that of the median plane calculation processing under imaging slice setting image acquisition processing. Hereinafter, a specific explanation will be given.

The imaging slice calculation section 244 binarizes the acquired imaging slice setting image (here, a median plane image) 520 to acquire the binarized image 521 (step S501). Then, the AC-PC line template 530 is extracted from the template group stored in the storage device (step S502). Then, template matching processing between the binarized image 521 and a template 530 is performed (step S503). Here, the same processing as the above-described median plane calculation processing is used as the template matching processing.

Then, an examination section 832 (here, AC-PC line) on the template 530 at the position in a matching state is set as an imaging slice on an imaging slice setting image (here, a median plane image) 820 (step S504). Then, the imaging slice calculation section 244 outputs it as a recommended imaging slice. In addition, the imaging slice calculation section 244 makes the UI control section 250 perform the recommended imaging slice calculation processing described above.

Figure 7:
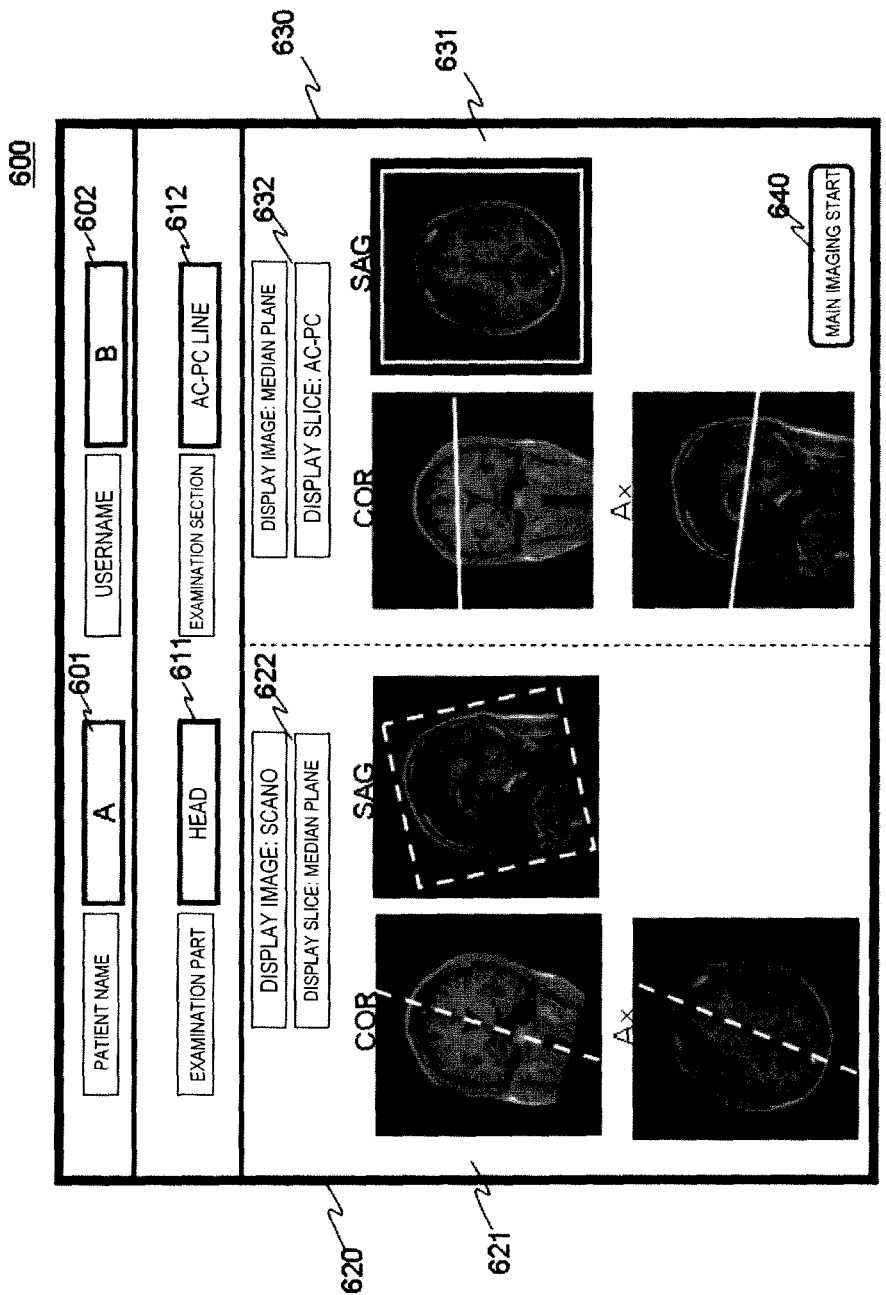
FIG. 7 is an example of a UI screen of the first embodiment.

Next, a user interface (UI) screen which is generated and displayed by the user interface (UI) control selection 250 will be described. FIG. 7 is an example of the UI screen 600 of the present embodiment. Although there is no step of displaying a scanogram image and an imaging slice setting section in the above process flow, a case where a scanogram image and an imaging slice setting section are displayed is illustrated herein. The image data for generating the UI screen 600 is stored in advance in the storage device.

As shown in this drawing, the UI screen 600 of the present embodiment has: a patient information input region 601 used to input the information which specifies a patient, for example, a patient name and the like; an operator information input region 602 used to input the information which specifies an operator, for example, an operator name and the like; an examination part information input region 611 used to input the information which specifies an examination part; an examination section information input region 612 used to input the information which specifies an examination section; an imaging slice setting image information display region 620 which displays the information regarding an imaging slice setting image; an imaging slice information display region 630 which displays the information regarding an imaging slice; and a main imaging start button display region 640 which receives an instruction to start main imaging from an operator.

The imaging slice setting image information display region 620 includes an imaging slice setting image display region 621 which displays a scanogram image acquired by the imaging slice setting image acquisition section and the information, which indicates the position of an imaging slice setting image set on the scanogram image, and an imaging slice setting image information display region 622 which displays the information specifying the contents displayed in the imaging slice setting image display region 621.

The imaging slice information display region 630 includes an imaging slice display region 631 which displays an imaging slice setting image and the information indicating the imaging slice position and an imaging slice information display region 632 which displays the information specifying the contents displayed in the imaging slice display region 631.

When the MRI apparatus 100 is started, the UI control section 250 generates the UI screen 600 and displays it on the display unit 108. The UI control section 250 receives an input from the operator to the patient information input region 601, the operator information input region 602, the examination part information input region 611, and the examination section information input region 612. The examination control section 210 starts an examination when the UI control section 250 receives the input.

In addition, when an instruction to display a scanogram image on the display unit 108 and the information regarding the imaging slice setting section stored in advance according to an examination part and the scanogram image are received from the imaging slice setting section 240, the UI control section 250 displays the received scanogram image and the received imaging slice setting section in the imaging slice setting image information display region 620.

In addition, when an instruction to display a recommended imaging slice on the display unit 108 and the information regarding the imaging slice are received from the imaging slice setting section 240, the UI control section 250 displays the imaging slice setting image and the information specifying the recommended imaging slice in the imaging slice information display region 630. When an instruction of recommended imaging slice calculation is received from the imaging slice setting section 240, the UI control section 250 calculates the recommended imaging slice and displays the imaging slice setting image and the information specifying the calculated recommended imaging slice in the imaging slice information display region 630.

In an example where the head AC-PC line of the present embodiment is an examination section, a scanogram image of each of the coronal, axial, and sagittal sections is displayed in the imaging slice setting image display region 621, and a line or plane which specifies the median plane is displayed on each image. In addition, the information indicating that the displayed image is a scanogram image and the displayed slice is a median plane is displayed in the imaging slice setting image information display region 622. In addition, a median plane image of each of the coronal, axial, and sagittal sections is displayed in the imaging slice display region 631, and the information indicating that the displayed image is a median plane image and the displayed slice is an AC-PC line is displayed in the imaging slice information display region 632.

Moreover, unlike the head AC-PC line, in the case of an examination section or an examination part in which the examination section can be directly designated on a scanogram image of each of the coronal, axial, and sagittal sections, the same information is displayed in the imaging slice setting image information display region 620 and the imaging slice information display region 630. Alternatively, in this case, the imaging slice setting image information display region 620 may not be provided.

Figure 8:
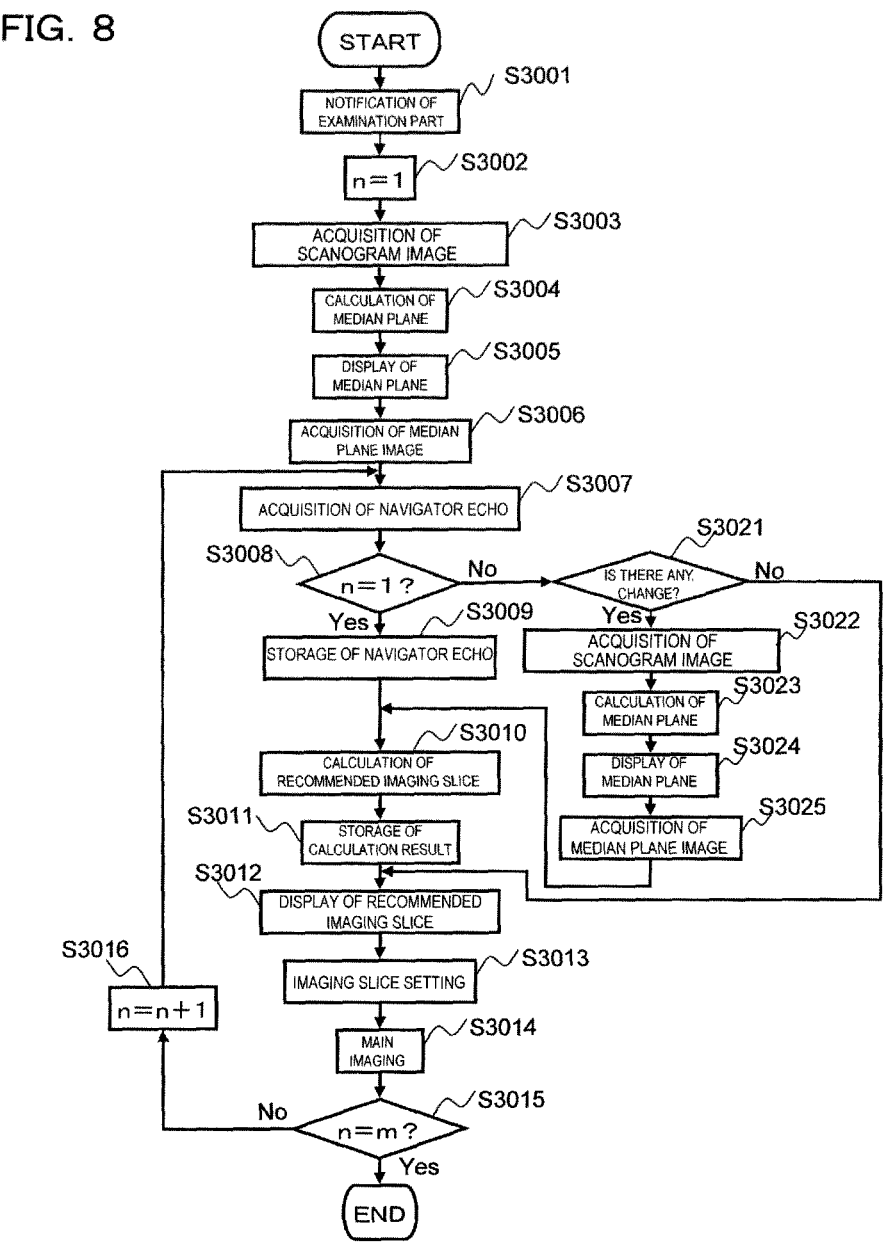
FIG. 8 is a process flow of examination processing when the AC-PC line of the head of the first embodiment is an examination section.

Here, the flow of examination processing by the examination control section 210 in the case of performing imaging with the AC-PC line of the head as an examination section as described above is shown in FIG. 8. In addition, an acquired image is shown in FIG. 9. Here, imaging is performed m times, and n is a counter which counts the number of times of imaging.

The UI control section 250 receives an input of imaging conditions including an designation of an imaging part (here, head AC-PC line) from the operator through the UI screen 600 (step S3001). When the UI control section 250 receives the input, the examination control section 210 starts processing. First, the examination control section 210 sets the counter n to 1 (step S3002) and makes the imaging slice setting section 240 set an imaging slice.

The imaging slice setting section 240 receives an instruction from the examination control section 210 and makes the imaging slice setting image acquisition section 241 acquire a scanogram image (step S3003). Then, as shown in FIG. 9(a), the imaging slice setting section 240 makes the imaging slice setting image acquisition section 241 perform the median plane calculation processing, which specifies the median plane 332, on the scanogram image 320 (step S3004). Here, the UI control section 250 displays the information, which specifies the median plane on the scanogram image, on the imaging slice setting image information display region 620 (step S3005). Then, an image of the acquired median plane is acquired (step S3006).

Then, the imaging slice setting section 240 makes the navigator echo acquisition section 242 acquire a navigator echo (step S3007). Then, it is determined whether or not the number of times of imaging is 1 (step S3008). If the number of times of imaging is 1, the acquired navigator echo is stored (step S3009). Then, as shown in FIG. 9(b), the imaging slice setting section 240 makes the imaging slice calculation section 244 calculate the recommended imaging slice (here, AC-PC line) 532 on the image 520 of the median plane (step S3010).

Then, the imaging slice setting section 240 stores the calculated recommended imaging slice in the storage device (step S3011) and makes the UI control section 250 display it on the imaging slice information display region on the UI image 600 (step S3012), and waits for an instruction from the operator. When an instruction to start main imaging is received from the operator through the main imaging start button display region 640, the imaging slice setting section 240 sets the recommended imaging slice calculated in step S3010 as an imaging slice of main imaging (step S3013).

In response to the imaging slice setting of the imaging slice setting section 240, the examination control section 210 executes main imaging (step S3014). In the main imaging, the imaging section 220 executes imaging of the imaging slice set according to the imaging sequence set in advance and the signal processing section 230 reconstructs an image from the acquired echo signal.

After the main imaging, the examination control section 210 determines whether or not all planned imaging has been finished (step S3015), and the examination processing is ended if al imaging is finished. On the other hand, if all imaging is not finished, the counter n is incremented by 1 (step S3016), and the process returns to step S3007.

In addition, when it is determined that the imaging is not first imaging in step S3008, the imaging slice setting section 240 makes the change determination section 243 determine whether or not the position of the subject 101 has been changed (step S3021). If there is no change, the process proceeds to step S3012 in which the imaging slice stored in the storage device is displayed again on the display unit 108, and the processing continues.

On the other hand, when it is determined that there is a change in step S316, the imaging slice setting section 240 makes the imaging slice setting image acquisition section 241 acquire an imaging slice setting image. Here, the imaging slice setting image acquisition section 241 acquires the scanogram image 320 first by performing scanogram imaging in the scanogram imaging slice determined according to a part (step S3022). Then, the imaging slice setting image acquisition section 241 performs median plane calculation processing for specifying the median plane 332 on the scanogram image 320 (step S3023). Here, the UI control section 250 displays the information, which specifies the median plane on the scanogram image, on the imaging slice setting image information display region 620 (step S3024). Then, the imaging slice setting image acquisition section 241 acquires the image 520 of the acquired median plane (step S3025). Then, after the image 520 of the median plane is acquired as an imaging slice setting image, the imaging slice setting section 240 proceeds to step S3010 to continue the processing.

Until now, the flow of examination control by the examination control section 210 in the case of performing imaging with the AC-PC line of the head as an examination section has been described.

As described above, according to the present embodiment, not only can an imaging slice be set automatically by designating an examination part, but also imaging can be performed by setting a desired examination section accurately as an imaging slice even if the subject 101 moves during the examination.

That is, according to the present embodiment, in an examination in which the same examination section is captured multiple times, a position change of the subject 101 is automatically recognized and an imaging slice is reset even if there is a change in the position of the subject 101 during the examination. In addition, the recognition of the displacement and the resetting of an imaging slice are performed in a short time. Therefore, according to the present embodiment, in the examination in which the same examination section is captured multiple times, the same examination section can be accurately captured without a significant increase in the examination time and an operation increase. In particular, even if the subject 101 moves during the examination, the same examination section can be captured each time without the influence.

According to the present embodiment, the possibility of acquiring images of the same examination section by the one-time examination flow is increased.

Therefore, no time is wasted in restarting. In addition, it is not necessary to acquire the 3D volume data which takes time in order to set the slice section. Therefore, according to the present embodiment, in the examination in which a plurality of images are acquired on the same examination section, an increase in an examination time can be suppressed without giving the excessive burden on the operator. As a result, since a plurality of images of the desired examination section can be acquired easily and accurately, examination efficiency can be improved.

Moreover, in the above-described embodiment, when it is determined that the position of the subject 101 has changed in step S2021 (in an example of the head AC-PC line, step S3021), scanogram imaging is executed again in the same scanogram imaging slice to acquire an imaging slice setting image. However, the present invention is not limited to this. Here, the scanogram imaging may also be performed such that the variation ($\Delta x$, $\Delta y$, $\Delta z$, $\Delta \phi$, $\Delta \theta$, $\Delta \rho$) calculated at the time of determination of the change determination section 243 is reflected.

The variation is reflected on a scanogram imaging slice, a template in which matching is performed, and the like. For example, scanogram imaging is performed by shifting a scanogram imaging slice by the calculated variation. Alternatively, although the median plane is further calculated from the scanogram image in the example of the head AC-PC line described above, each point of a median plane template 730 used herein is displaced by the value to perform matching.

For example, when the variation in the x direction is $\Delta x$ and the variation in the y direction is $\Delta y$, the value Px, y of a point (x, y) of the median plane template 730 is set as the value of a point (x+$\Delta x$, y+$\Delta y$) to perform matching. Pi in the above-described Expressions (1) and (2) is expressed as follows.

$$P_{i+\Delta x} = (P_{i+\Delta x,\ 1+\Delta y},\ P_{i+\Delta x,\ 2-\Delta y},\ \ldots,\ P_{i+\Delta x,\ n+\Delta y})$$

In addition, in the example of the head AC-PC line described above, imaging slice setting image acquisition processing (processing of steps S3003 to S3006 or processing of steps S3022 to S3025) may be repeated multiple times in order to specify the median plane more accurately.

Figure 10:
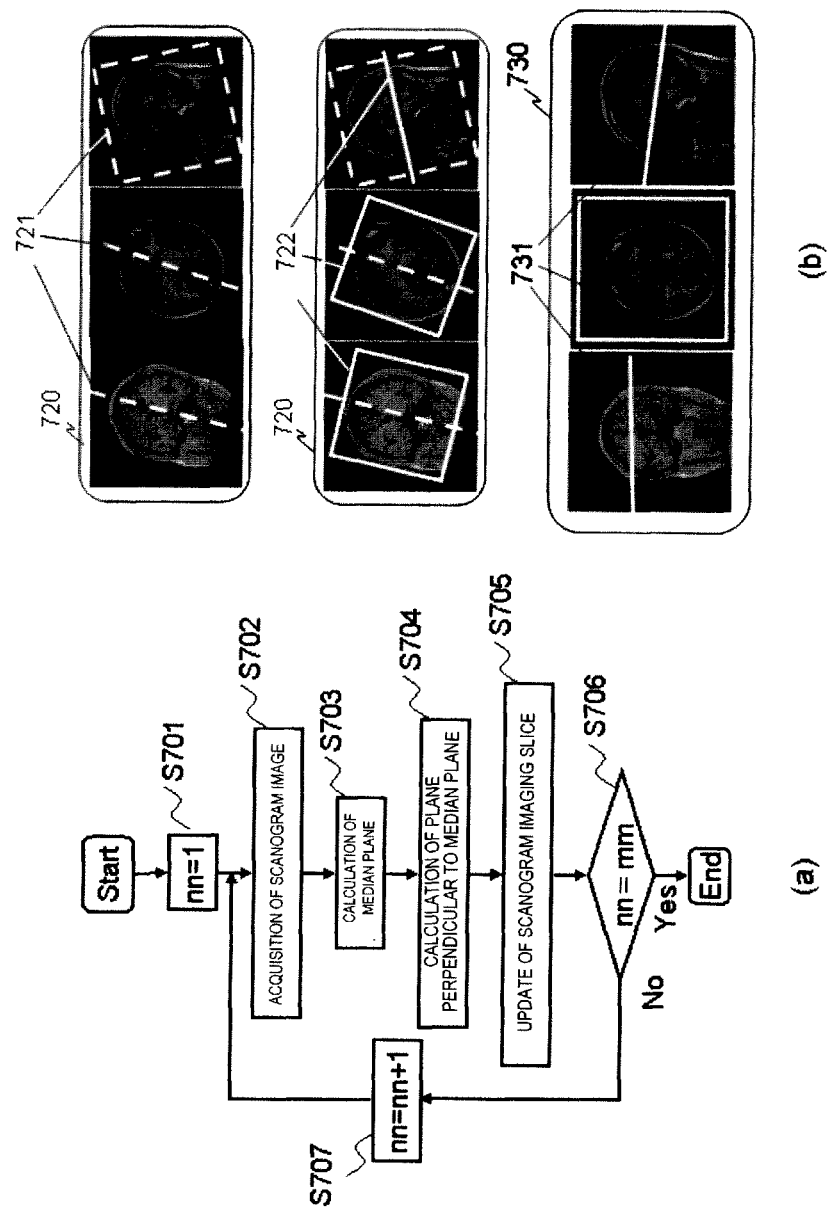
FIG. 10 is a view for explaining another example of imaging slice setting processing of the first embodiment, where FIG. 10(*a*) is the process flow and FIG. 10(*b*) is an example of an acquired image.

The situation of processing in this case is shown in FIG. 10. FIG. 10(a) is a process flow of imaging slice setting image acquisition processing when the imaging slice setting image acquisition processing are repeated multiple times, and FIG. 10(b) is an image acquired in the course of processing. Here, it is assumed that the imaging slice setting image acquisition processing are repeated mm (mm is an integer of 1 or more). In addition, nn is a counter.

First, the imaging slice setting image acquisition section 241 sets the counter nn to 1 (step S701). Then, scanogram imaging is performed in a scanogram imaging slice set at this point of time (step S702). In first scanogram imaging, a scanogram imaging slice stored in advance so as to match an examination part is used. Then, a median plane 721 is calculated on the acquired scanogram image 720 (step S703). Then, a plane 722 perpendicular to the acquired median plane 721 is calculated (step S704). The calculated plane 722 is set as a new scanogram imaging slice (step S705), and the process returns to step S702 and the processing is repeated a number of times (mm times) set in advance (steps S706 and S707). Through the above procedure, the accuracy in determining the median plane 721 can be improved. The imaging slice setting image acquisition section 241 can acquire the image 730 of the determined median plane 721 and set an imaging slice (here, AC-PC line) 731 for main imaging more accurately.

In addition, a recommended imaging slice calculated by the imaging slice calculation section 244 may be adjusted by the operator. An input of the adjustment is received through the imaging slice information display region 630 of the UI screen 600, for example. An operator sets an imaging slice at a desired position on the imaging slice setting image, which is displayed in main imaging slice information display region 630 together with the recommended imaging slice, using a mouse, a keyboard, or the like of the operating unit 107. The imaging slice setting section 240 receives an input of the amount of adjustment from the operator and sets it as an imaging slice after changing the recommended imaging slice.

In addition, it is possible to provide a function of reflecting the received amount of adjustment on the template used when setting the imaging slice. That is, the template is updated by reflecting the received amount of adjustment on the information of the template indicating the positional relationship between a characteristic part and an examination section set as an imaging slice. For example, in the AC-PC line template 530 of the median plane image, the position of an examination section (here, AC-PC line) 532 with respect to the characteristic part 531 is adjusted finely.

As a result, since a more accurate template can be acquired, it is possible to accurately position the desired imaging slice. In addition, a configuration capable of selecting whether to reflect the amount of adjustment on a template may be set. That is, only when the operator selects reflecting the amount of adjustment, the received amount of adjustment is reflected on the template.

In addition, although the template is stored for every part and every examination section in the present embodiment, the present invention is not limited to this. For example, the template may be stored for every part and examination section and for every patient and/or every operator. In this case, an input of the information, which specifies a patient and/or an operator, and the information, which specifies an examination part and an examination section, through the UI screen 600 by the operator is received, and each processing section extracts this information from a template database.

These templates for every operator and every patient are created in advance for every operator and every patient and are stored in a template database. Moreover, it is also possible to create templates without distinguishing operators, patients, and the like first and to register the templates so as to be distinguished for every operator and for every patient at the time of updating using the technique described above. If templates are stored for every patient, an imaging slice can be accurately set when imaging the same examination section of the same subject 101 repeatedly at intervals as in the postoperative follow-up examination.

In addition, if the position of the subject 101 is displaced only within the specific plane, main imaging may be performed in an imaging slice set by the first imaging without performing the imaging slice setting image acquisition processing again. The displacement within the specific plane refers to a case where only the amount of displacement in one axial direction or two axial directions, among $\Delta x$, $\Delta y$, and $\Delta z$, exceeds the threshold value.

Figure 11:
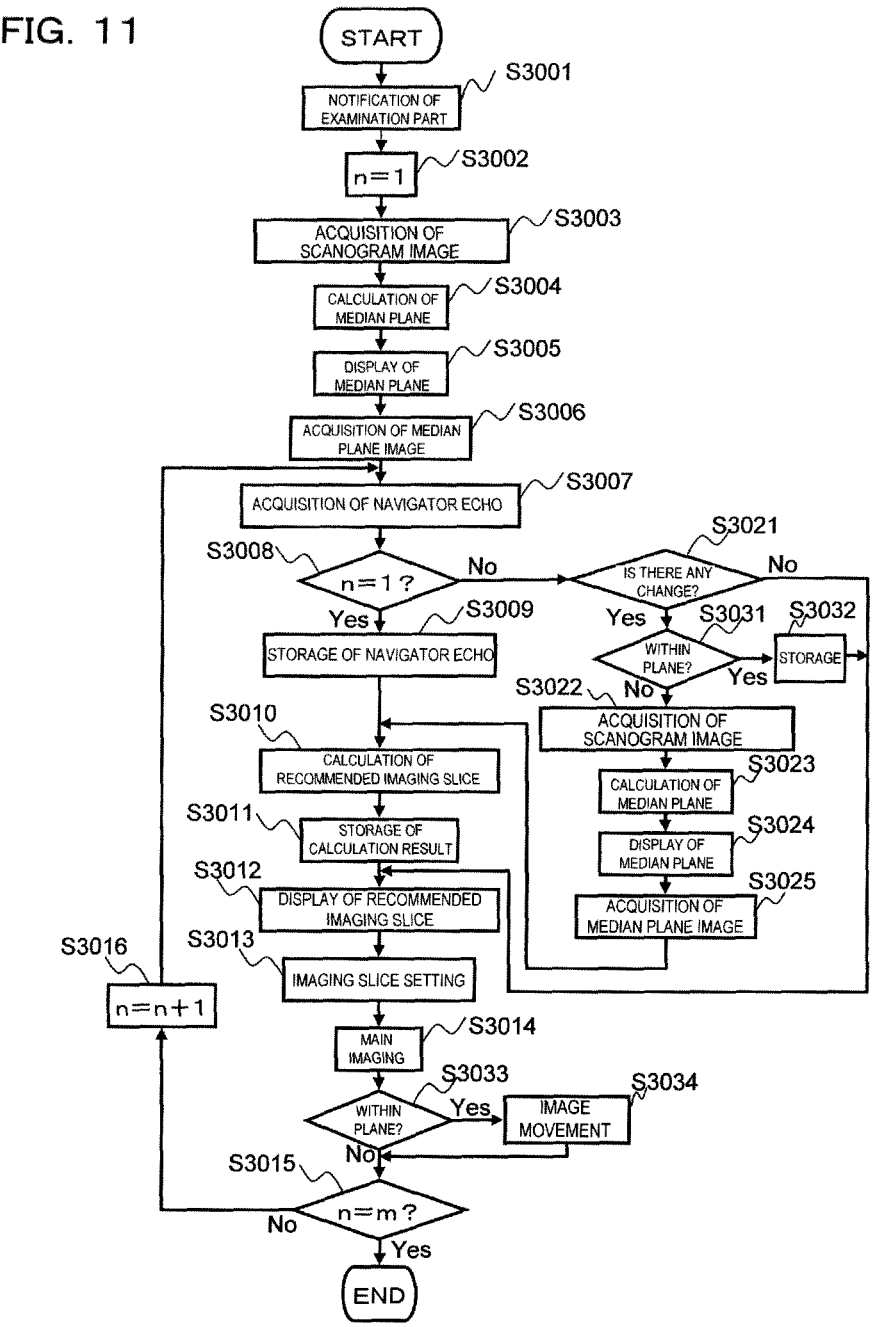
FIG. 11 is a process flow of another example of the examination processing of the first embodiment.

The flow of examination processing in this case is shown in FIG. 11. Here, a case of imaging the AC-PC line of the head as in the above embodiment will be described as an example. The flow of the examination processing in this case is basically the same as in FIG. 8. Here, the same reference numeral is given to the same processing as in FIG. 8. However, in main processing, the imaging slice setting section 240 makes the change determination section 243 determine whether or not the position of the subject 101 has been changed in step S3021, and makes the change determination section 243 determine whether or not the change has occurred only within the plane after it is determined that there is a change (step S3031). Then, when it is determined that the change is not only the movement within the plane, the process proceeds to step S3022. On the other hand, when it is determined that the change is only the movement within the plane, the information indicating that there is only the movement within the plane and the amount of displacement are stored (step S3032), and the process proceeds to step S3012. Moreover, after the main imaging in step S3014, the examination control section 210 determines whether or not the information indicating that there is the movement within the plane is stored (step S3033). If the information indicating that there is the movement within the plane is stored, the examination control section 210 makes the signal processing section 230 move a reconstructed image by the stored amount of displacement (step S3034), and the process proceeds to step S3013. As shown in FIG. 12, the user interface control section 250 displays an image 840, which is obtained by displacing a reconstructed image 830 by the stored amount of displacement, on the display unit 108. On the other hand, if the information indicating that there is movement within the plane is not stored, the process proceeds to step S3015.

In addition, when the displacement of the position of the subject 101 occurs only within the specific plane, a recommended imaging slice for main imaging may be calculated by shifting it by the amount of displacement without displacing the reconstructed image. The flow of examination processing in this case is shown in FIG. 13. Here, a case of imaging the AC-PC line of the head as in the above embodiment will be described as an example. The flow of the examination processing in this case is basically the same as in FIG. 3, and the same reference numeral is given to the same processing. However, in main processing, the imaging slice setting section 240 makes the change determination section 243 determine whether or not the position of the subject 101 has been changed in step S3021, and makes the change determination section 243 determine whether or not the change has occurred only within the plane after it is determined that there is a change (step S3031). Then, when it is determined that the change is not only the movement within the plane, the process proceeds to step S3022. On the other hand, when it is determined that the change is only the movement within the plane, the imaging slice setting section 240 makes the imaging slice calculation section 244 calculate an imaging slice shifted by the amount of displacement from the recommended imaging slice, which is stored in the storage device, as a new recommended imaging slice (step S3041). Then, the process returns to step S3011.

Moreover, for a change of the position of the subject 101, the position in the first imaging is set as a reference and it is determined whether or not there is a change by comparison with this position in the embodiment described above. However, the method of determining whether or not there is a change is not limited to this. For example, whether or not there is a change may also be determined by comparison with the position in the last imaging.

Figure 14:
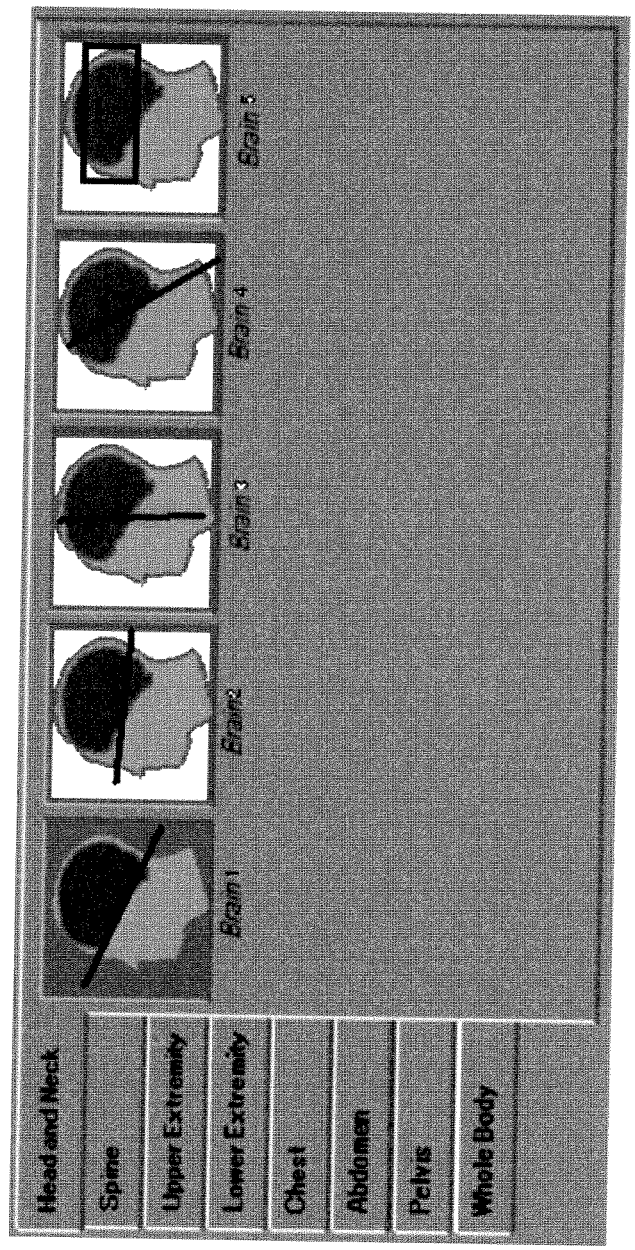
FIG. 14 is a view for explaining another example of a UI screen of the first embodiment.

In addition, although an examination part and an examination section are input through the UI screen 600 in the present embodiment, the present invention is not limited to this. For example, an examination part and an examination section may be input from a graphical display 650 as shown in FIG. 14.

In addition, although the case of an examination of the head AC-PC line has been described as an example in the present embodiment, the part to be examined is not limited to this. Moreover, in the case of an examination of the head AC-PC line, since it is not possible to set the examination section directly from a scanogram image of each of the axial, coronal, and sagittal sections, a median plane image is calculated as an imaging slice setting image as described above. However, in the case of an examination of a part in which the examination section can be set directly on a scanogram image of any one of the axial, coronal, and sagittal sections, a scanogram image acquired by scanogram imaging is set as an imaging slice setting image as it is.

Figure 15:
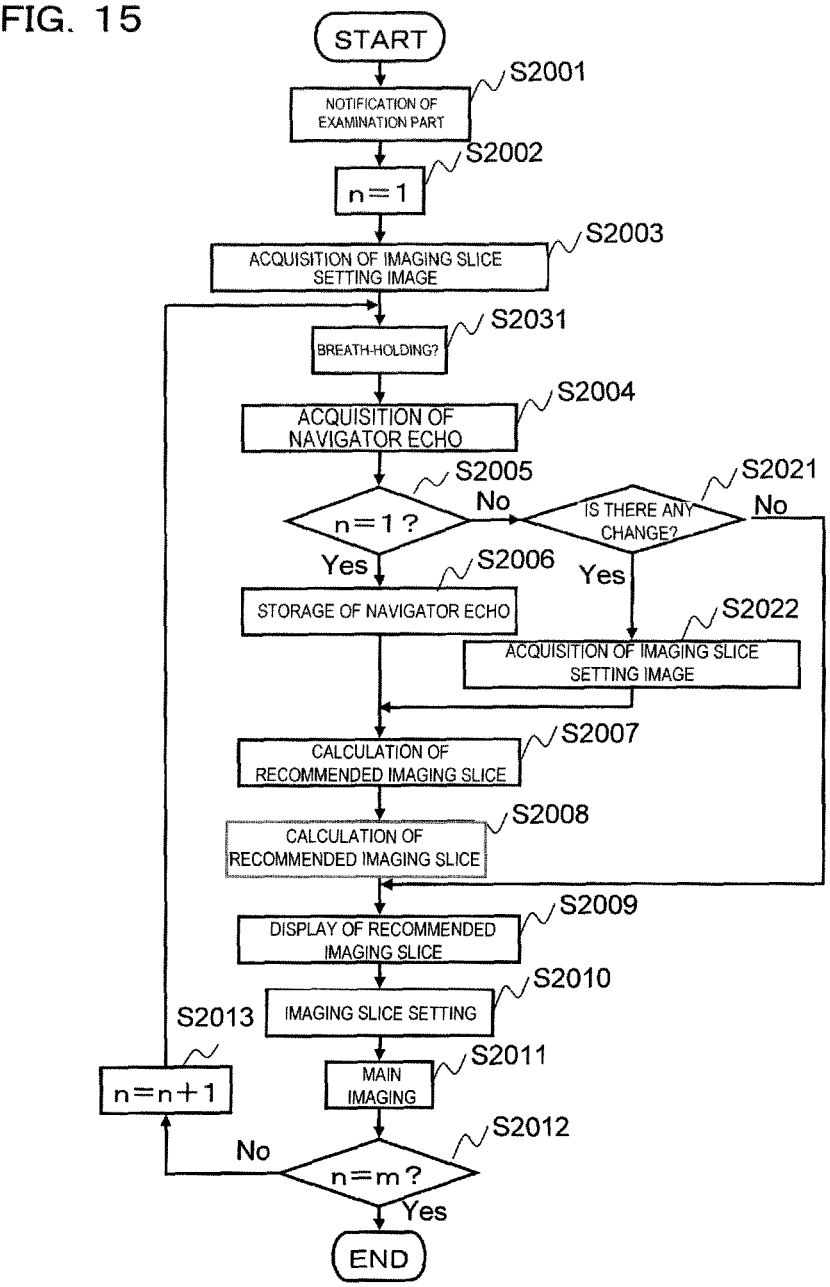
FIG. 15 is a process flow of another example of the examination processing of the first embodiment.

According to the present embodiment, even if the examination part is a part with large motion such as respiratory motion, for example, the heart or the abdomen, the present embodiment can meet it. As an example, the process flow of examination processing when performing multi-slice short-axis imaging of the heart by breath-holding multiple times is shown in FIG. 15. This process flow is basically the same as the flow of the above processing shown in FIG. 2, and the same reference numeral is given to the same processing. However, the imaging slice setting section 240 acquires a navigator echo after the subject 101 holds the breath according to an instruction of the operator (step S2003). Breath-holding of the subject 101, that is, an instruction of the completion of breath-holding is received through the UI screen 600 or the operating unit 107.

Figure 16:
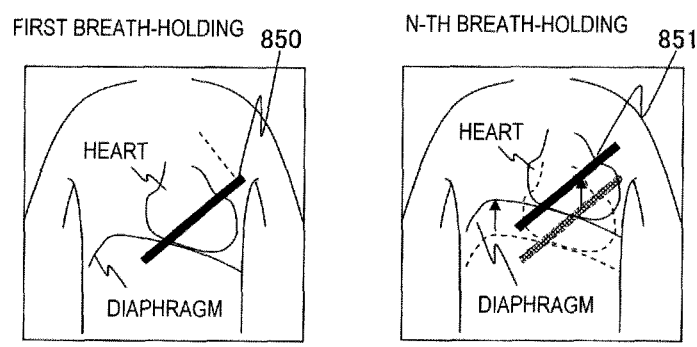
FIG. 16 is a view for explaining another example of the examination processing of the first embodiment.

For example, a difference (displacement) in the breath-holding level is detected by acquiring a navigator echo of the diaphragm changed by respiratory motion. By adjusting an imaging slice by the amount of displacement using any method described above, the same examination section as an imaging slice 850 in the first imaging can be set as an imaging slice 851 in the next n-th imaging as shown in FIG. 16.

Therefore, according to the present embodiment, even if there is not only body motion but also a difference in the breath-holding level in imaging performed multiple times for a part with respiratory motion or the like, the examination section determined in advance can be set as an imaging slice for every imaging. In addition, without using breath-holding, the examination section determined in advance for every imaging can be set as an imaging slice similarly under free breathing.

Second Embodiment

Next, a second embodiment to which the present invention is applied will be described. In the present embodiment, the present invention is applied to a kinematic examination in which imaging is performed multiple times while changing the position. In the present embodiment, in the kinematic examination, a desired examination section is imaged even if there is a position change. The MRI apparatus of the present embodiment has basically the same configuration as the first embodiment. Hereinafter, the present embodiment will be described focusing on a different configuration from the first embodiment.

Figure 17:
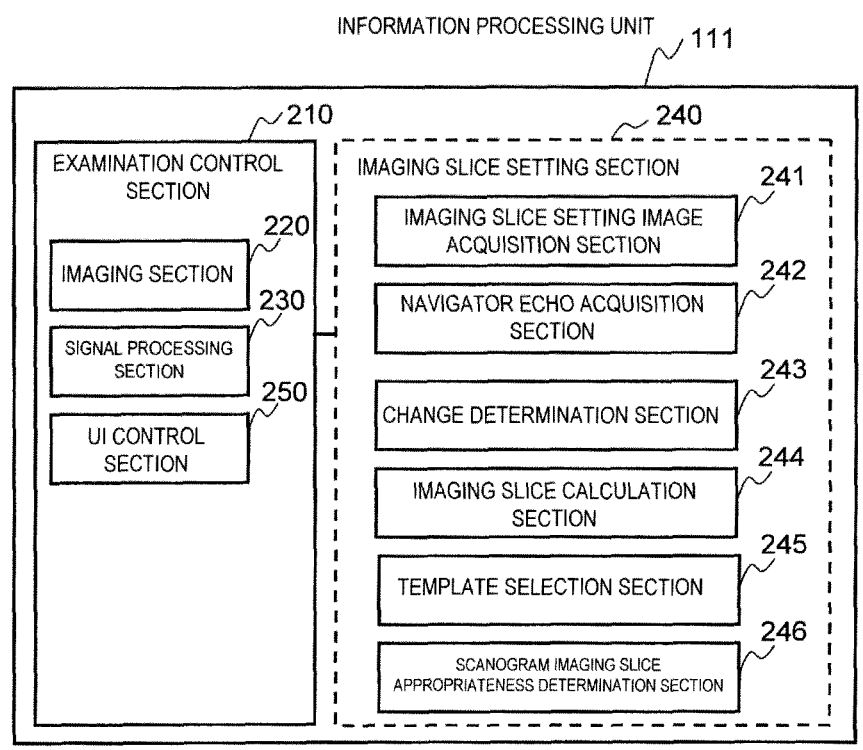
FIG. 17 is a functional block diagram of an information processing unit of an MRI apparatus of a second embodiment.

FIG. 17 is a functional block diagram of the information processing unit 111 of the present embodiment. Here, the same reference numeral is given to the same functional configuration as in the first embodiment. As shown in this drawing, the examination control section 210 of the information processing unit 111 of the present embodiment realizes the imaging slice setting section 240 by the imaging section 220, the signal processing section 230, and the UI control section 250. Moreover, the imaging slice setting section 240 includes a template selection section 245 and a scanogram imaging slice appropriateness determination section 246 in addition to the configuration of the first embodiment.

In the present embodiment, a kinematic examination is performed. An object part in the kinematic examination is a movable part, and the positional relationship between a characteristic part and an examination section of an examination part is not fixed. Accordingly, a plurality of movable-mode templates are prepared. The template selection section 245 of the present embodiment selects a template, which is most suitable for a state of the subject 101 at the time of imaging, from the plurality of different movable-mode templates prepared according to the examination part. The template selection section 245 makes the UI control section 250 perform template selection processing.

In addition, in the present embodiment, since an examination part is a movable part as described above, a scanogram imaging slice registered in the storage device so as to match the examination part (and the examination section) is not necessarily optimal. The scanogram imaging slice appropriateness determination section 246 evaluates the appropriateness of a scanogram imaging slice in which an imaging slice setting image is acquired. This evaluation is performed by pattern matching. According to the evaluation, the imaging slice setting section 240 makes the imaging slice setting image acquisition section 241 acquire an imaging slice setting image again using the acquired imaging slice as a scanogram imaging slice. The scanogram imaging slice appropriateness determination section 246 makes the UI control section 250 perform determination.

In addition, in the first embodiment, the change determination section 243 basically sets a first navigator echo as the navigator echo, which is a reference in determining whether or not there is a displacement. In the present embodiment, however, a navigator echo acquired immediately before the last imaging is set as the reference navigator echo since this is a kinematic examination. In addition, although a comparison is performed using pattern matching or absolute value data in the first embodiment, a signal value profile is used in the present embodiment. Details thereof will be described later.

In addition, the UI control section 250 of the present embodiment has an interface which receives from an operator an instruction indicating that changing the angle of the knee has been finished for every imaging, that is, preparation for the next imaging has been completed.

Figure 18:
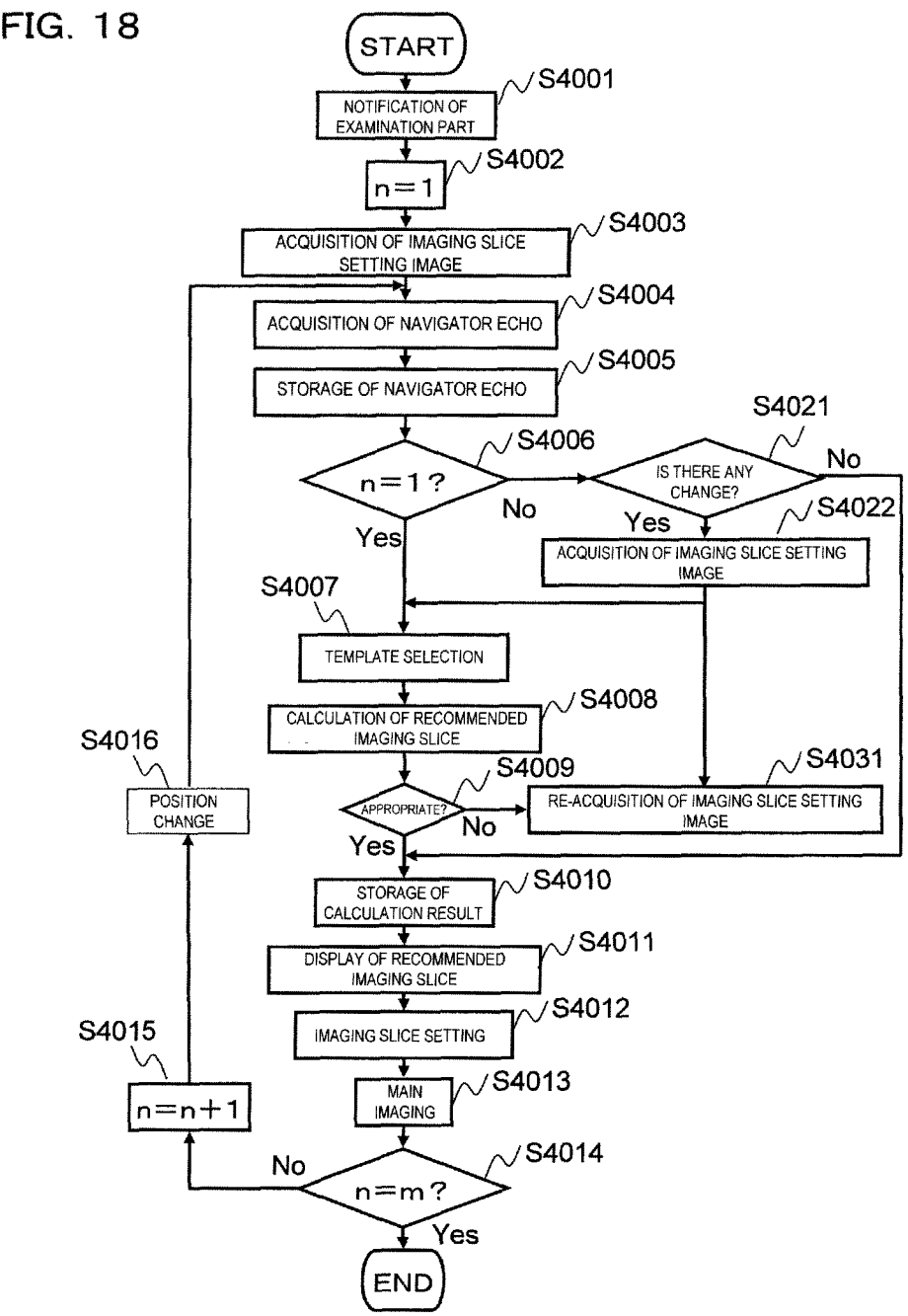
FIG. 18 is a process flow of examination processing of the second embodiment.

Here, the flow of examination processing by the examination control section 210 of the present embodiment will be described. FIG. 18 is a process flow of examination processing of the present embodiment. Here, similar to the first embodiment, it is assumed that an imaging slice matching the examination section is set for every imaging and imaging is performed m (m is a positive integer) times in an examination in which imaging is performed multiple times. In addition, n (n is a positive integer) is a counter which counts the number of times of imaging. In addition, the following examination is executed according to the control of the examination control section 210 of the present embodiment.

When an operator's designation of an examination part (and an examination section) is received through the UI screen 600, the UI control section 250 notifies the examination control section 210 and the imaging slice setting section 240 of the examination part (and the examination section) (step S4001). The examination control section 210 starts examination processing according to the reception of the notification from the UI control section 250. First, the examination control section 210 sets the counter n to 1 (step S4002) and makes the imaging slice setting section 240 set an imaging slice.

The imaging slice setting section 240 makes the imaging slice setting image acquisition section 241 acquire an imaging slice setting image in a scanogram imaging slice stored according to the examination part and the examination section received by the UI control section 250 (step S4003). Then, the imaging slice setting section 240 makes the navigator echo acquisition section 242 acquire a navigator echo (step S4004), stores it in the storage device so as to match the number of times of imaging (n) at that point of time (step S4005). Then, the imaging slice setting section 240 determines the number of times of imaging (step S4006). If the imaging is first imaging, the imaging slice setting section 240 proceeds to template selection processing to make the template selection section 245 select a template which is used to calculate a recommended imaging slice (step S4007). Then, the imaging slice calculation section 244 is made to calculate a recommended imaging slice for main imaging on the imaging slice setting image using the selected template (step S4008).

Then, the imaging slice setting section 240 makes the scanogram imaging slice appropriateness determination section 246 determine the appropriateness of the calculation result (step S4009). When it is determined that the calculation result is appropriate, the calculation result is stored in the storage device as an n-th recommended imaging slice (step S4010), and the calculation result is also displayed on the display unit 108 as a recommended imaging slice (step S4011). Then, the imaging slice setting section 240 waits for an instruction from the operator to set the recommended imaging slice as an imaging slice (step S4012).

In response to the imaging slice setting of the imaging slice setting section 240, the examination control section 210 executes main imaging in the imaging slice (step S4013).

Then, the examination control section 210 determines whether or not all imaging, which is due to be performed in the examination, has been executed (step S4014). If all imaging is finished, the processing ends. On the other hand, if all imaging is not finished, the counter n is incremented by 1 (step S4015), and an instruction of the completion of position change from the operator is waited for. When the instruction of change completion is received from the operator (step S4016), the process returns to step S4004 to continue the processing.

In addition, when it is determined that the imaging is not first imaging in step S4006, the imaging slice setting section 240 makes the change determination section 243 determine whether or not the position of the subject 101 has been changed (step S4021). Here, when it is determined that there is no change, the process proceeds to step S4010 in which an imaging slice in the previous (n−1)-th imaging slice stored in the storage device is stored as an n-th imaging slice, and the processing continues. On the other hand, when it is determined that there is a change in step S4021, the imaging slice setting section 240 makes the imaging slice setting image acquisition section 241 acquire an imaging slice setting image (step S4022). Then, the process proceeds to step S4007 to continue the processing.

In addition, when it is determined that the calculation result is not appropriate in step 4009, the imaging slice setting section 240 makes the imaging slice setting image acquisition section 241 perform imaging slice setting image re-acquisition processing for acquiring an imaging slice setting image using the recommended imaging slice calculated in step S4008 as a scanogram imaging slice (step S4031), and the process proceeds to step S4007 to continue the processing.

Hereinafter, specific processing which is different from the processing in the above first embodiment will be described through an example of a kinematic examination (kinematic imaging) of the knee joint. The axial plane perpendicular to the patella is set as the examination section, and the angle of the knee is changed for each imaging. In addition, since the part to be examined is a movable part, a plurality of templates according to the movement situation are stored in the storage device so as to match the examination part (and the examination section).

First, the imaging slice setting image acquisition processing of step S4003 by the imaging slice setting image acquisition section 241 of the present embodiment will be described. As described above, in the present embodiment, the examination section is the axial plane perpendicular to the patella. Accordingly, the imaging slice setting image is a scanogram image (sagittal scanogram image) of the sagittal plane on which the patella portion has been captured. Here, scanogram imaging of the scanogram imaging slice, which is stored so as to match the examination part, is performed in advance to acquire the sagittal scanogram image.

Then, the change determination processing of step S4021 by the change determination section 243 of the present embodiment will be described using FIG. 19. In addition, in the present embodiment, the navigator echo acquisition section 242 acquires navigator echoes in three axial directions perpendicular to each other, that is, in the x-axis direction, the y-axis direction, and the z-axis direction according to the known imaging sequence for navigator echo acquisition.

The change determination section 243 of the present embodiment determines whether or not there is a change by comparing the position ((n−1)-th position) 1001 immediately before the last imaging with the position (n-th position) 1002 immediately before the current imaging. In the present embodiment, an image changes with each imaging since the angle of the knee is intentionally changed. Therefore, since it is not possible to perform determination with a change between before-and-after navigator echoes in each axial direction, the determination is performed using a signal value profile. Here, only a change on the xy plane will be considered and described as an example.

Figure 19:
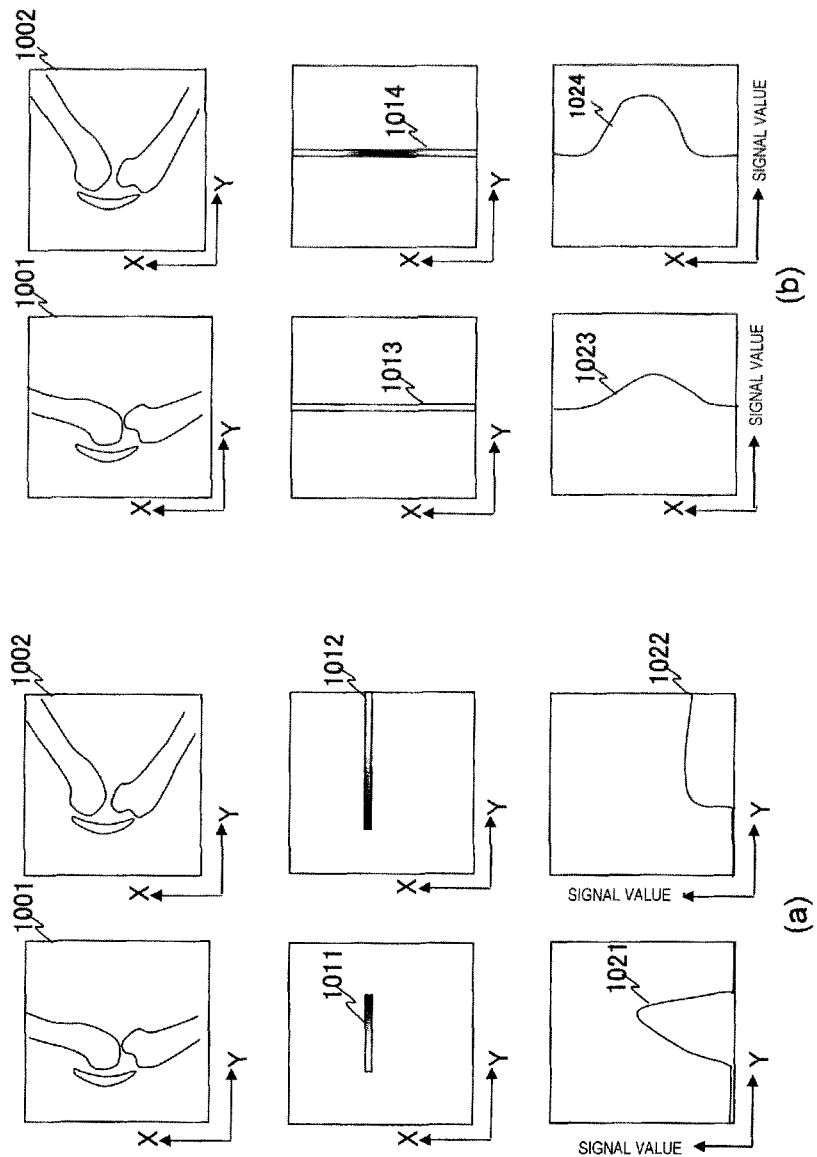
FIG. 19 is a view for explaining change determination processing of the second embodiment.

FIG. 19($a$) is a view for explaining a method of determining whether or not there is a change in the y-axis direction. A signal value profile 1021 of absolute value data 1011 obtained by y-axis-direction Fourier transform of a navigator echo acquired in a state of the (n−1)-th position 1001 is compared with a signal value profile 1022 of absolute value data 1012 obtained by y-axis-direction Fourier transform of a navigator echo acquired in a state of the n-th position 1002.

FIG. 19($b$) is a view for explaining a method of determining whether or not there is a change in the x-axis direction. A signal value profile 1023 of absolute value data 1013 obtained by x-axis-direction Fourier transform of a navigator echo acquired in a state of the (n−1)-th position 1001 is compared with a signal value profile 1024 of absolute value data 1014 obtained by x-axis-direction Fourier transform of a navigator echo acquired in a state of the n-th position 1002.

The comparison is performed using a simple difference or the like. That is, an average value of difference values of the points of the signal profiles 1021 and 1022 having the same y coordinate is calculated. Then, the calculated average value is compared with the threshold value set in advance. Similarly, the average value of difference values of the points of the signal profiles 1023 and 1024 having the same x coordinate is calculated. Then, the calculated average value is compared with the threshold value set in advance. The same processing is performed for the Z direction. Then, when it is determined as the comparison result that the calculated average value exceeds the threshold value in at least one direction of the x-axis direction, the y-axis direction, and the z-axis direction, the change determination section 243 determines that there is a change. If the calculated average value is equal to or smaller than the threshold value in all of the directions, the change determination section 243 determines that there is no change.

In addition, since the examination in the present embodiment is a kinematic examination, the position of the subject 101 changes for every imaging. However, since it is determined whether or not there is a change using a threshold value as described above, it is determined there is no change when the amount of change is small.

Next, the template selection processing in step S4007 by the template selection section 245 of the present embodiment will be described. As described above, in the present embodiment, the sagittal plane including the patella is used as the imaging slice setting image. Here, the axial plane perpendicular to the patella which is the examination section is determined by template matching. On the sagittal plane including the patella, characteristic parts are a patella, a femur, and a tibia. However, since the knee joint which combines these is a movable joint, the positional relationship between the patella, the femur, and the tibia changes. In particular, since the examination in the present embodiment is a kinematic examination, the positional relationship is made to change intentionally. For this reason, in the present embodiment, a plurality of knee joint sagittal templates in which angles between the femur and the tibia are different are prepared, and a knee joint sagittal template closest to the shape of the examination part on the acquired imaging slice setting image is selected as an optimal knee joint sagittal template from the plurality of knee joint sagittal templates and this is used for template matching.

Specifically, the template selection section 245 calculates D, which is expressed by Expression (1) or (2), using the method described above to thereby obtain Dmin in each matching state. That is, the template selection section 245 binarizes the imaging slice setting image first and calculates D expressed by Expression (1) or (2) while moving each knee joint sagittal template by one pixel at a time on the image after binarization, and sets the case of Dmin as the minimum as a matching state for each knee joint sagittal template. Then, the template selection section 245 selects the knee joint sagittal template with the smallest value of Dmin as an optimal knee joint sagittal template.

In addition, although the degree of matching is determined in the entire knee joint sagittal template herein, the present invention is not limited to this. For example, the degree of matching may be determined for each part of the knee joint, such as a patella, a femur, and a tibia, and a part with the overall highest degree of matching may be selected. As an example, a case of selecting the patella or the femur with the higher degree of matching will be described using FIG. 20.

Figure 20:
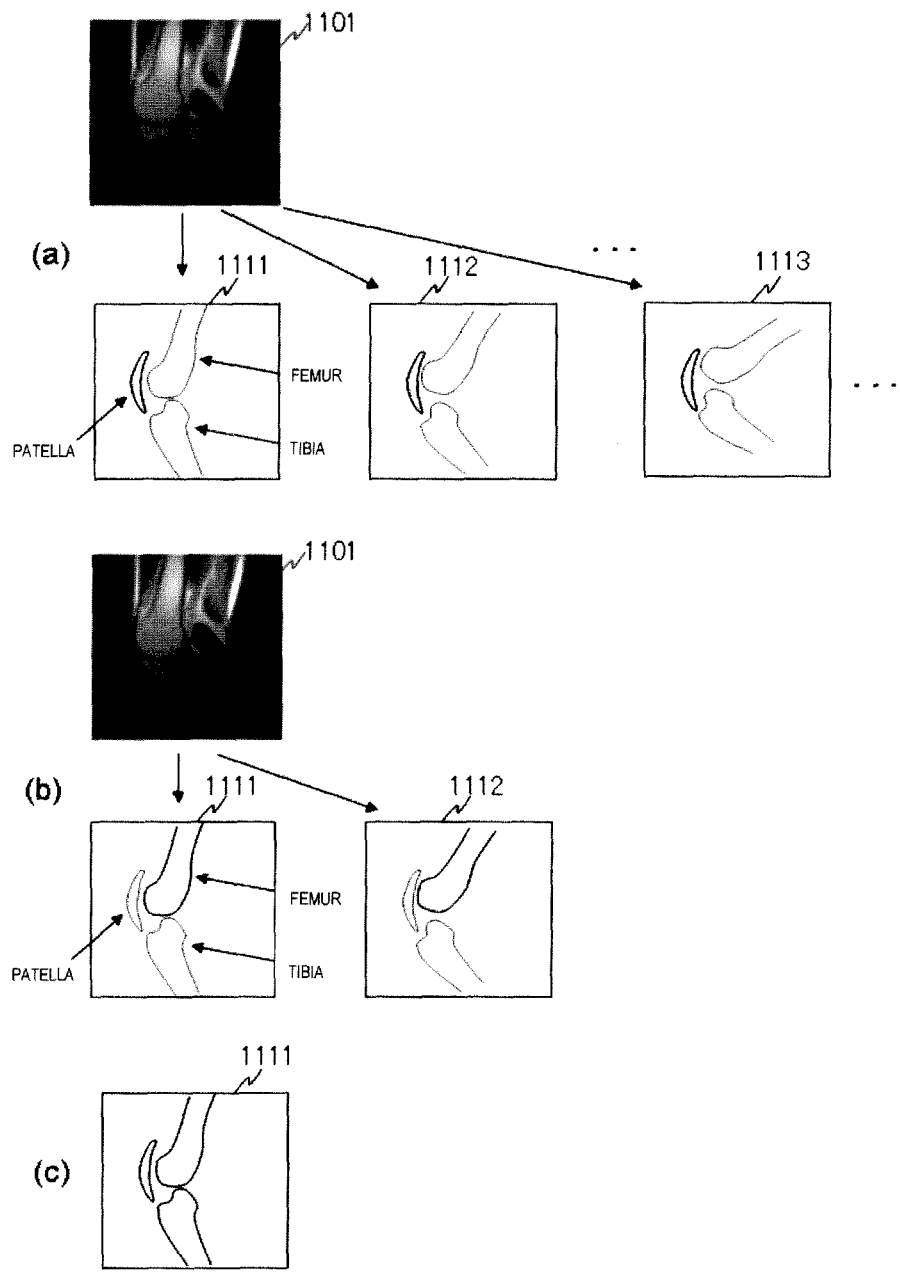
FIG. 20 is a view for explaining template selection processing of the second embodiment.
Figure 22:
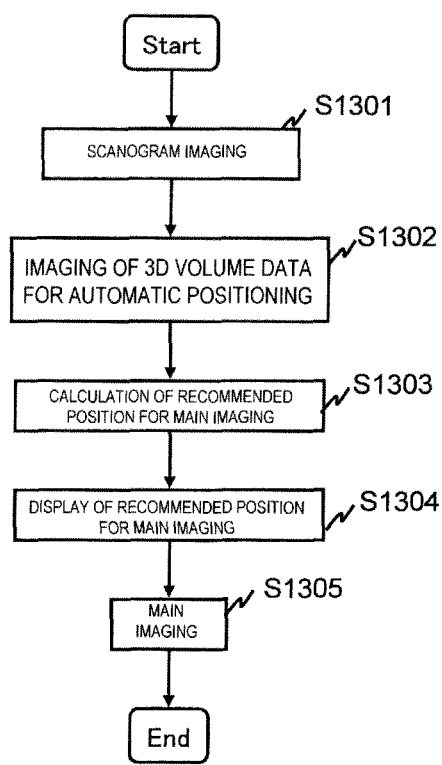
FIG. 22 is a process flow of the imaging slice setting procedure in the related art.
Figure 23:
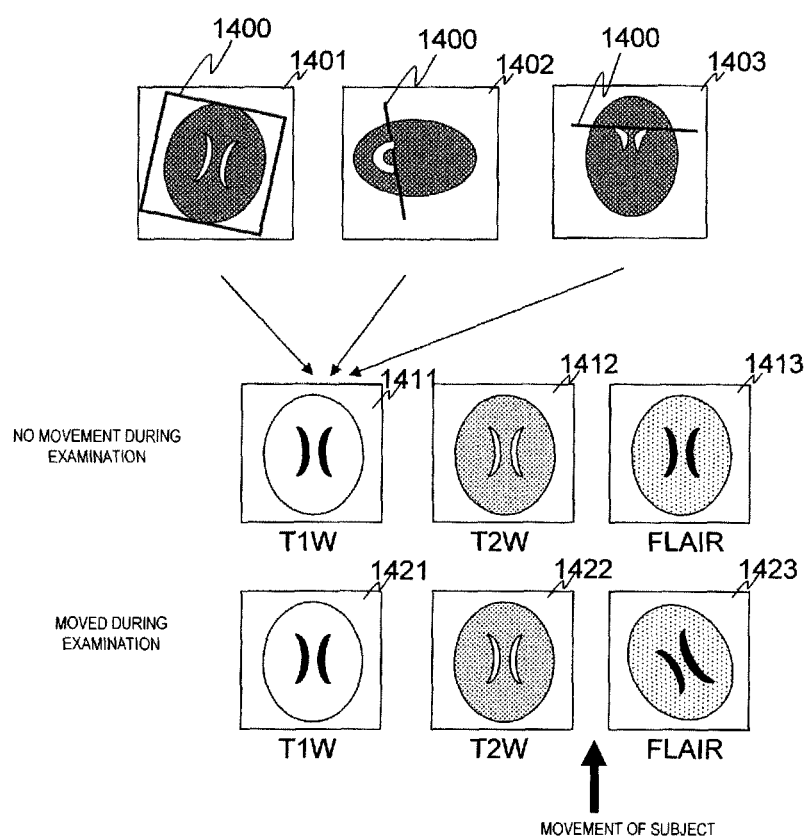
FIG. 23 is a view for explaining a problem in an examination including a plurality of imagings.

First, as shown in FIG. 20(*a*), the template selection section 245 binarizes an imaging slice setting image and selects the knee joint sagittal template with the high degree of matching among a plurality of prepared knee joint sagittal templates 1111, 1112, 1113, . . . . Here, it is assumed that the knee joint sagittal templates 1111 and 1112 are selected. Then, as shown in FIG. 20(*b*), the template selection section 245 selects one of the selected knee joint sagittal templates 1111 and 1112 which has the highest degree of matching in a range set in advance in which femur portions match each other. Here, it is assumed that the knee joint sagittal template 1111 is selected.

This is set as an optimal knee joint sagittal template as a selection result. In addition, such selection is determined by calculating the above Expression (1) or (2).

In addition, in the appropriateness determination of the above step S4009 by the scanogram imaging slice appropriateness determination section 246, Dmin calculated by the template selection processing of the described template selection section 245 is used. The scanogram imaging slice appropriateness determination section 246 determines that the scanogram imaging slice is appropriate if Dmin is equal to or smaller than the threshold value set in advance.

Next, details of the imaging slice setting image re-acquisition processing of the above step S4031 by the imaging slice setting image acquisition section 241 will be described. This processing is a processing for acquiring an imaging slice setting image again when it is determined that the scanogram imaging slice is inappropriate in step S4009. When it is determined that the scanogram imaging slice is inappropriate in the determination of step S4009, it is thought that the scanogram imaging slice set in advance is not appropriate for the current position and there is mismatching in the inclination with respect to the axis of the subject 101 in the imaging slice setting image itself. Accordingly, a more appropriate imaging slice setting image is acquired by changing the scanogram imaging slice.

Here, the flow of the entire processing for calculating a recommended imaging slice accurately by repeating imaging slice setting image re-acquisition processing until it is determined that the scanogram imaging slice is appropriate in the above step S4009 will be described. FIG. 21 is a view for explaining the above-described processing including the imaging slice setting image re-acquisition processing by the imaging slice setting image acquisition section 241 in step S4031. FIG. 21(*a*) is the process flow, and FIG. 21(*b*) is a template used and an image acquired.

First, the template selection section 245 selects a template 1220 (step S4007). Using the selected template and an imaging slice setting image 1230 at that point of time, the imaging slice calculation section 244 calculates an examination section 1122 as the recommended imaging slice 1231 by template matching (step S4008). Then, the scanogram imaging slice appropriateness determination section 246 calculates the above Dmin and determines the appropriateness of the imaging slice setting image (step S4009).

When it is determined that the imaging slice setting image is inappropriate in step S4009, the imaging slice setting section 240 makes the imaging slice setting image acquisition section 241 perform imaging slice setting image re-acquisition processing. Specifically, the imaging slice setting image acquisition section 241 acquires an axial image 1240 by performing scanogram imaging with the recommended imaging slice 1231 calculated in step S4008 as the scanogram imaging slice (step S1201).

Then, the imaging slice setting image acquisition section 241 makes the template selection section 245 select a template 1221 on the axial image 1240 using the same method as in step S4007 (step S1202). Then, using the template 1221 and the axial image 1240, the imaging slice calculation section 244 is made to calculate a cross section 1223 as a scanogram imaging slice 1241 by template matching (step S1203). Then, the imaging slice setting image acquisition section 241 acquires a sagittal image 1250 by performing scanogram imaging of the scanogram imaging slice 1241 calculated in step S1203 (step S1204).

Then, the process returns to step S4007 in which the template selection section 245 selects a template (step S4007). The imaging slice calculation section 244 calculates a recommended imaging slice 1251 by template matching (step S4008), and the scanogram imaging slice appropriateness determination section 246 determines the appropriateness (step S4009).

When it is determined that the scanogram imaging slice is appropriate in step S4009, the acquired recommended imaging slice 1251 is stored (step S4010), and the recommended imaging slice 1251 and the sagittal image 1250 which is an imaging slice setting image at that point of time are displayed (step S4011). Then, the examination control section 210 acquires a reconstructed image 1260 by performing main imaging using the recommended imaging slice 1251 as an imaging slice.

As described above, according to the present embodiment, the imaging slice setting image re-acquisition processing is repeated until Dmin becomes equal to or smaller than the threshold value. Therefore, even if the position of the subject 101 changes greatly for every imaging as in the kinematic examination, an imaging slice setting image at the time of imaging can be acquired accurately.

According to the present embodiment, since a position change of the subject 101 is automatically recognized in an examination, in which the same examination section is captured multiple times, as in the first embodiment, an imaging slice can be reset in a short time without requiring complicated processing. Therefore, according to the present embodiment, in the examination in which a plurality of images are acquired on the same examination section, an increase in an examination time can be suppressed without giving an excessive burden on the operator. As a result, since a plurality of images of the desired examination section can be acquired easily and accurately, examination efficiency can be improved.

In addition, according to the present embodiment, an imaging slice setting image at the time of imaging can be accurately acquired even in the kinematic examination as described above. Therefore, according to the present embodiment, images of a desired examination section can be accurately acquired in the kinematic examination in which the shape of an object to be examined changes for every imaging.

In addition, although a navigator echo in each imaging is stored in a storage device herein, only a navigator echo in last imaging and the newest navigator echo may be stored since the comparison for determining whether or not there is a displacement is a comparison with a navigator echo in the last imaging as described above.

On the contrary, in the first embodiment, it may be determined whether or not there is a change using the signal profile of a navigator echo described in the present embodiment.

REFERENCE SIGNS LIST

100: MRI apparatus
101: subject
102: static magnetic field generator
103: gradient magnetic field coil
104: RF coil
105: RF probe
106: signal detector
107: operating unit
108: display unit
109: gradient magnetic field power source
111: information processing unit
112: bed
210: examination control section
220: imaging section
230: signal processing section
240: imaging slice setting section
241: imaging slice setting image acquisition section
242: navigator echo acquisition section
243: change determination section
244: recommendation imaging slice calculation section
245: template selection section
246: scanogram imaging slice appropriateness determination section
250: user interface control section
320: scanogram image
321: binarized image
330: median plane template
331: characteristic part
332: median plane
401: position immediately before first imaging
402: position immediately before n-th imaging
411: absolute value data
412: absolute value data
421: absolute value data
422: absolute value data
431: navigator echo image
432: navigator echo image
441: navigator echo image
442: navigator echo image
451: navigator echo image
452: navigator echo image
520: median plane image
521: binary image
530: AC-PC line template
531: characteristic part
532: AC-PC line
600: UI image
601: patient information input region
602: operator information input region
611: examination part information input region
612: examination section information input region
620: imaging slice setting image information display region
621: imaging slice setting image display region
622: imaging slice setting image information display region
630: imaging slice information display region
631: imaging slice display region
632: imaging slice information display region
640: main imaging start button display region
650: graphical display
720: scanogram image
721: median plane
722: plane perpendicular to the median plane
730: median plane image
731: AC-PC line
830: reconstructed image
840: reconstructed image
850: imaging slice
851: imaging slice
1001: position
1002: position
1011: absolute value data
1013: absolute value data
1014: absolute value data
1021: signal value profile
1022: absolute value data
1022: signal value profile
1023: signal value profile
1024: signal value profile
1101: sagittal scanogram image
1111: knee joint sagittal template 1112: knee joint sagittal template
1113: knee joint sagittal template
1220: knee joint sagittal template
1221: knee joint axial template
1230: sagittal scanogram image
1231: recommendation imaging slice
1240: axial scanogram image
1241: scanogram imaging slice
1250: sagittal scanogram image
1251: recommendation imaging slice
1260: reconstructed image
1400: imaging slice
1401: axial scanogram image
1402: sagittal scanogram image
1403: coronal scanogram image
1411: T1W image
1412: T2W image
1413: FLAIR image
1421: T1W image
1422: T2W image
1423: FLAIR image

The invention claimed is:

1. A magnetic resonance imaging apparatus comprising:
a slice setting section which sets an imaging slice to be imaged; and
an imaging section which performs imaging of the imaging slice set by the slice setting section,
wherein the slice setting section includes:
a slice setting image acquisition section which acquires an imaging slice setting image for calculating a recommended imaging slice according to an examination part and an examination section;
a recommended slice calculation section which calculates a recommended imaging slice on the imaging slice setting image whenever the slice setting image acquisition section acquires the imaging slice setting image;
a body movement information acquisition section which acquires body movement information for every imaging; and
a change determination section which determines whether or not there is a change in a position of a subject on the basis of the acquired body movement information, and
the slice setting image acquisition section acquires the imaging slice setting image again when the change determination section determines that there is a change,
wherein the recommended slice calculation section binarizes the imaging slice setting image and calculates the recommended imaging slice by performing template matching between the binarized imaging slice setting image and a template which is a template registered in advance according to the examination part and the examination section and which specifies the relationship between the examination section and an anatomical characteristic part on the imaging slice setting image.

2. The magnetic resonance imaging apparatus according to claim 1, further comprising:
an interface section for interface with an operator,
wherein the interface section receives the examination part and the examination section, displays the recommended imaging slice, and receives an operator's instruction to adjust the recommended imaging slice, and
the slice setting section reflects the adjustment on the recommended imaging slice.

3. The magnetic resonance imaging apparatus according to claim 2, wherein the slice setting image acquisition section acquires a scanogram image of a cross section, which is set in advance according to the examination part and the examination section received through the interface section, and acquires the imaging slice setting image from the scanogram image.

4. The magnetic resonance imaging apparatus according to claim 1, wherein
the change determination section calculates the amount of change further, and
when the change determination section determines that there is a change, the slice setting image acquisition section acquires the imaging slice calculation image again by reflecting the amount of change.

5. The magnetic resonance imaging apparatus according to claim 1, further comprising:
an appropriateness determination section which determines the appropriateness of a plane where the slice setting image acquisition section has acquired the imaging slice setting image,
wherein the slice setting image acquisition section acquires an imaging slice setting image with the recommended imaging slice as an imaging slice when the appropriateness determination section determines that the plane is inappropriate.

6. The magnetic resonance imaging apparatus according to claim 1, wherein
the body movement information acquisition section acquires body movement information before executing each imaging, and
the change determination section determines whether or not there is a change in the position of the subject by comparing body movement information acquired before the imaging with body movement information acquired before a first time of one imaging from the imaging.

7. The magnetic resonance imaging apparatus according to claim 1, wherein
the body movement information acquisition section acquires body movement information before executing each imaging, and
the change determination section determines whether or not there is a change in the position of the subject by comparing body movement information acquired before the imaging with body movement information acquired before previous imaging.

8. The magnetic resonance imaging apparatus according to claim 1, wherein the recommended slice calculation section further includes a template selection section which selects a template, which is used in the template matching, using the imaging slice setting image whenever the slice setting image acquisition section acquires the imaging slice setting image.

9. The magnetic resonance imaging apparatus according to claim 1,
wherein the body movement information acquisition section acquires body movement information in each of three axial directions perpendicular to each other and a body movement information image on each of three cross sections perpendicular to each other, and
the change determination section determines whether or not there is a position change by calculating a parallel movement component of the position change from the body movement information in each of the three axial directions perpendicular to each other and calculating a rotational movement component of the position change from the body movement information image on each of the three cross sections perpendicular to each other.

10. The magnetic resonance imaging apparatus according to claim 1,
wherein the imaging part is a head, and
the imaging slice calculation image is a median plane.

11. The magnetic resonance imaging apparatus according to claim 2, further comprising:
a template update section which reflects the operator's instruction to adjust the imaging slice on a template used when calculating the recommended imaging slice on the imaging slice calculation image.

12. A method performed by a magnetic resonance imaging apparatus, the method comprising:
a slice setting step of setting an imaging slice to be imaged;
an imaging step of performing imaging of the imaging slice set by the slice setting step;
a slice setting image acquisition step of acquiring an imaging slice setting image for calculating a recommended imaging slice according to an examination part and an examination section;
a recommended slice calculation step of calculating a recommended imaging slice on the imaging slice setting image whenever the slice setting image acquisition step acquires the imaging slice setting image;
a body movement information acquisition step of acquiring body movement information for every imaging;
a change determination step of determining whether or not there is a change in a position of a subject on the basis of the acquired body movement information,
wherein the slice setting image acquisition step acquires the imaging slice setting image again when the change determination step determines that there is a change, and
wherein the recommended slice calculation step binarizes the imaging slice setting image and calculates the recommended imaging slice by performing template matching between the binarized imaging slice setting image and a template which is a template registered in advance according to the examination part and the examination section and which specifies the relationship between the examination section and an anatomical characteristic part on the imaging slice setting image.

* * * * *